US007803577B2

(12) United States Patent
Weiss

(10) Patent No.: US 7,803,577 B2
(45) Date of Patent: Sep. 28, 2010

(54) TROPOELASTIN DERIVATIVES

(75) Inventor: Anthony S. Weiss, Sydney (AU)

(73) Assignee: University of Sydney, Sydney, New South Wales (AU)

( * ) Notice: Subject to any disclaimer, the term of this patent is extended or adjusted under 35 U.S.C. 154(b) by 0 days.

(21) Appl. No.: 11/880,320

(22) Filed: Jul. 20, 2007

(65) Prior Publication Data
US 2008/0039397 A1 Feb. 14, 2008

Related U.S. Application Data

(63) Continuation of application No. 11/053,710, filed on Feb. 8, 2005, now abandoned, which is a continuation of application No. 09/463,091, filed on Mar. 31, 2000, now Pat. No. 7,193,043.

(51) Int. Cl.
*C12N 15/00* (2006.01)
(52) U.S. Cl. ............ 435/69.1; 435/7.1; 435/320.1; 435/325; 530/350
(58) Field of Classification Search ............... None
See application file for complete search history.

(56) References Cited

U.S. PATENT DOCUMENTS

| 5,726,040 | A | 3/1998 | Ensley et al. | |
|---|---|---|---|---|
| 5,969,106 | A | 10/1999 | Rothstein et al. | |
| 6,232,458 | B1 * | 5/2001 | Weiss et al. | 536/23.5 |
| 6,451,326 | B2 | 9/2002 | Ensley | |
| 6,808,707 | B2 | 10/2004 | Ensley | |
| 7,001,328 | B1 | 2/2006 | Barofsky et al. | |

FOREIGN PATENT DOCUMENTS

| JP | 01-235472 | 9/1989 |
|---|---|---|
| JP | 186989/90 | 7/1990 |
| WO | WO94/14958 | 7/1994 |
| WO | WO99/03886 | 1/1999 |

OTHER PUBLICATIONS

Fazio et al. (Sequence Alignment, Accession No. X52896, Dec. 16, 1994).*
Tassabehji et al, Human Molecular Genetics, "*An Elastin Gene Mutation Producing Abnormal Tropoelastin and Abnormal Elastic Fibres in a Patient with Autosomal Dominant Cutis Laxa*", vol. 7, No. 6, 1998, pp. 1021-1028.
Canadian office Action, dated Jan. 9, 2008.
Indik et al. 1987 *P.N.A.S. USA* 84:5680-5684.
Indik et al. 1987 *Connect. Tissue Res.* 16:197-211.
Frangiskakis et al. 1996 *Cell* 86:59-69.
Fazio et al. 1988 *Lab. Invest.* 58:270-277.
Fazio et al. 1988 *J. Invest. Dermatol.* 91:458-464.
Osborne et al. 1996 *Genomics* 36:328-336.
Bashir et al. 1989 *J. Biol. Chem.* 264:8887 to 8891.
Indik et al. 1990 *Arch. Biochem. Biophys.* 280:80-66.
Oliver et al. 1987 *Collagen Res.* 7:77-89.
Sambrook, J., Fritsch, E.F., and Maniatis, T. 1989 in "Molecular Cloning: A Laboratory Manual", 2nd ed. Cold Spring Harbour Laboratory Press, Cold Spring Harbor, New York.
Bressnam et al. 1987 *Biochem.* 26:1497-11503.
Raju et al. 1987 *J. Biol. Chem.* 262:5755-5762.
Pierce et al. 1992 *Genomics* 12:651-658.
Lipman et al. 1985 *Science* 227:1435.
Hernan et al, Biochemistry, *Human Hemoglobin Expression in Escherichia coli: Importance of Optimal Codon Usage*, vol. 31, 1992, pp. 8619-8628.
Cappello et al, Biotechnol Prog, *Genetic Engineering of Structural Protein Polymers*, vol. 6, 1990, pp. 198-202.
Reiser et al, F.A.S.E.B., *Enzymatic and Nonenzymatic Cross-Linking of Collagen and Elastin*, vol. 6, pp. 2439-2449.
Sharp et al, Nucleic Acids Research, *The Coldon Adaptation Index—A Measure of Dirctional Synonymous Coldon Usage Bias and its Potential Applications*, vol. 15, No. 3, 1987, pp. 1281-1295.
Sechler et al, CIBA Foundation Symposium, *Elastin Gene Mutations in Transgenic Mice*, vol. 192, 1995, pp. 148-165.
Boyd et al, Matrix, *Mammalian Tropoelastin: Multiple Domains of the Protein Define an Evolutionary Divergent Amino Acid Sequence*, vol. 11, 1991, pp. 235-241.
Hernan et al, Biochemistry, *Human Hemoglobin Expression in Escherichia coli: Importance of Optimal Codon Usage*, vol. 31, 1992, pp. 8619-8628.
Newgard et al, Proc. Natl. Acad. Sci. USA, *Sequence Analysis of the cDNA Encoding Human Liver Glycogen Phosphorylase Reveals Tissue-Specific Codon Usage*, vol. 83, Nov. 1986, pp. 8132-8136.
Knorr et al, Tetrahedron Letters, *New Coupling Reagents in Peptide Chemistry*, vol. 30, 1989, pp. 1927-1930.
Ewart et al, Nature Gentics, *Hemizygosity at the Elastin Locus in a Developmental Disorder, Williams Syndrome*, vol. 5, Sep. 1993, pp. 11-16.
Foster et al, American Physiological Society, *The Regulation of Lung Elastin Synthesis*, vol. 259, 1990, pp. L13-L23.
R.B. Merrifield, Journal of American Chemistry Society, *Solid Phase Peptide Synthesis. I. The Synthesis of a Tetrapeptide*, vol. 85, Jan. 31, 1963, pp. 2149-2154.
Janne et al, Annals of Medicine, *Transgenic Animals as Bioproducers of Therapeutic Proteins*, vol. 24, 1992, pp. 273-280.
Slack et al, Molecular and Cellular Biology, *An Upstream Regulatory Region Mediates High-Level, Tissue-Specific Expression of the Human αl (I) Collagen Gene in Transgenic Mice*, vol. 11, Apr. 1991, pp. 2066-2074.
Sandberg et al, Methods in Enzymology, *Production and Isolation of Soluble Elastin from Copper-Deficient Swine*, vol. 82, 1982, pp. 657-665.

(Continued)

*Primary Examiner*—Hope A Robinson
(74) *Attorney, Agent, or Firm*—Nikolai & Mersereau, P.A.; C. C. Mersereau

(57) ABSTRACT

The invention relates to derivatives of tropoelastin and variants of those derivatives. The invention further provides expression products and hybrid molecules of the derivatives and variants of the invention. The invention further provides methods for the production of the derivatives, variants, expression products and hybrid molecules. Further provided are formulations, cross-linked structures and implants comprising the derivatives, variants, expression products and hybrid molecules of the invention. Further provided are uses of the derivatives, variants, expression products and hybrid molecules of the invention.

7 Claims, 34 Drawing Sheets

OTHER PUBLICATIONS

Bullock et al, Biotechniques, *XL1-Blue: A High Efficiency Plasmid Transforming recA Escherichia coli Strain with Beta-Galactosidase Selection*, vol. 5, No. 4, 1987, pp. 376-379.

Frangiskakis et al., Cell, *LIM-kinase1 Hemizygosity Implicated in Impaired Visuospatial Constructive Cognition*, vol. 86, Jul. 12, 1996, pp. 59-69.

Mecham et al, Biochemistry, *Trypsin-Like Neutral Protease Associates with Soluble Elastin*, vol. 16, No. 17, 1977, pp. 3825-3831.

Pierce et al, Genomics, *Elements of the Rat Tropoelastin Gene Associated with Alternative Splicing*, vol. 12, 1992, pp. 651-658.

Hayashi et al, Biochim, Biophys., *Presence of Elastin-related 45-kDa Fragment in Culture Medium Specific Cleavage Product of Tropoelastin in Vascular Smooth Muscle Cell Culture*, vol. 1244, 1995, pp. 325-330.

Franzblau et al, Journal of Biology Chemistry, *Role of Tropoelastin Fragmentation in Elastogenesis in rat Smooth Muscle Cells*, vol. 264, No. 25, Sep. 5, 1989, pp. 15115-15119.

Grosso et al, Archives of Biochemistry and Biophysics, *PGAIPG, a Repeated Hexapeptide of Bovine and Human Tropoelastin, Is Chemotactic for Neutrophils and Lewig Lung Carcinoma Cells*, vol. 305, No. 2, Sep. 1993, pp. 401-404.

McPherson et al, Biotechnol. Prog., *Production and Purification of a Recombinant Elastomeric Polypeptide, G-(VPGVG)$_{19}$ VPGV, from Eschericia coli*, vol. 8, 1992, pp. 347-352.

Kahari et al, Journal of Biological Chemistry, *Deletion Analysis of 5'—Flanking Region of the Human Elastin Gene*, vol. 265, 1990, pp. 9485-9490.

Parks et al, Matrix, *Cellular Expression of Tropoelastin mRNA Splice Variants*, vol. 1992, pp. 156-162.

Parks et al, American Journal of Respiratory Cell Molecular biology, *Tropoelastin Heterogeneity: Implications for Protein Function and Disease*, vol. 2, 1990, pp. 399-406.

Rosenbloom et al, CIBA Foundation Symposium, *Structure of the Elastin Gene*, vol. 192, 1995, pp. 59-80.

Rosenbloom et al, "Critical Review in Eukaryotic Gene Expression" CRC Press Inc.Expression, *Elastin Genes and Regulation*, vol. 1, 1990, pp. 145-156.

Zhang et al, Gene, *Low-usage Codons in Escherichia coli, Yeast, Fruit Fly and Primates*, vol. 105, 1991, pp. 61-72.

Eyre, Ann. Rev. Biochem. *Cross-Linking in Collagen and Elastin*, vol. 53, 1984, pp. 717-748.

Murray et al, Nucleic Acids Research, *Condon Usage in Plant Genes*, vol. 17, No. 2, 1989, pp. 477-498.

Indik et al, Archives of Biochemistry and Biophysics, *Production of Recombinant Human Tropoelastin: Characterization and Demonstration of Immunologic Chemotactic Activity*, vol. 280, No. 1, Jul. 1990, pp. 80-86.

Olliver et al, Collagen Rel. Research, *The Gene Coding for Tropoelastin is Represented as a Single Copy Sequence in the Haploid Sheep Genome*, vol. 7, 1987, pp. 77-89.

Sambrook et al, Molecular Cloning: A Laboratory Manual, 2$^{nd}$ ed.Cold Spring Harbour Laboratory Press, Cold Spring Harbour, New York, 1989.

Bressan et al, Biochem., *Repeating Structure of Chick Tropoelastin Revealed by Complementary DNA Cloning*, vol. 26, No. 6, Mar. 24, 1987, pp. 1497-1503.

Raju et al, Journal of Biological Chemistry, *Primary Structures of Bovine Elastin a, b, and c Deduced from the Sequences of cDNA Clones*, vol. 262, 1987, pp. 5755-5762.

Lipman et al, Science, *Rapid and Sensitive Protein Similarity Searches*, vol. 227, 1985, pp. 1435-1441.

Bedell-Hogan et al, Journal of Biological Chemistry, *Oxidation, Cross-linking, and Insolubilization of Recombinant Tropoelastin by Purified Lysyl Oxidase*, vol. 268. No. 14, May 15, 1993, pp. 10345-10350.

Marigo et al, Connective Tissue Research, *Mapping of Binding Sites for monoclonal Antibodies to Chick Tropoelastin by Recombinant DNA Techniques*, vol. 28, 1992, pp. 13-28.

Uitto et al, Biochemical Society Transactions, *Molecular Biology and Pathology of Human Elastin*, vol. 19, 1991, pp. 824-829.

Grosso et al, Biochemical Journal, *Fibroblast Adhesion to Recombinant Tropoelastin Expressed as a Protein A-fusion Protein*, vol. 273, 1991, pp. 517-522.

Foster et al, International Review of Connective Tissue Research, *Elastin Gene Expression*, vol. 10, 1983, pp. 65-95.

European Examination Report dated Nov. 18, 2005.

Wu et al, Journal of Biological Chemistry, *Glycosaminoglycans Mediate the Coacervation of Human Tropoelastin through Dominant Charge Interactions*, vol. 274, 1999, pp. 21719-21724.

Canadian Examination Report dated Sep. 30, 2005.

Kenyon et al, Journal of Biological Chemistry, *A Novel Human cDNA with a Predicted Protein Similar to Lysyl Oxidase Maps to Chromosome 15q24-q25*, vol. 268, 1993, pp. 18435-18437.

Hamalainen et al, Genomics, *Structure of the Human Lysyl Oxidase Gene*, vol. 27, 1993, pp. 544-548.

Fornieri et al, Journal of ELL Biology, *Lysyl Oxidase Activity and Elastin/Glycosaminoglycan Interactions in Growing Chick and Rat Aortas*, vol. 105, Sep. 1987, pp. 1463-1469.

Bedell-Hogan et al, Journal of Biological Chemistry, *Oxidation, Cross-linking, and Insolubilization of Recombinant Tropoelastin by Purified Lysyl Oxidase*, vol. 268, No. 14, 1993, pp. 10345-10350.

Beck von Bodman et al, Proc. Natl. Acad. Sci. USA, *Synthesis, Bacterial Expression, and Mutagenesis of the Gene Coding for Mammalian Cytochrome $b_5$*, vol. 83, 1986, pp. 9443-9447.

McGowan et al, American Journal of Physiology, *Serine Proteinase Inhibitors Infulence the Stability of Tropoelastin mRNA in Neonatal Rat Lung Fibroblast Cultures*, vol. 270, 1996, pp. L376-L385.

Davidson et al, Methods in Enzymology, *Regulation of Elastin Synthesis in Organ and Cell Culture*, vol. 144, pp. 214-232.

Hinek et al, Journal of Cell Biology, *67-kD Elastin-binding Protein is a Protective "Companion" of Extracellular Insoluble Elastin and Intracellular Tropoelastin*, vol. 126, No. 2, Jul. 1994, pp. 563-574.

Chang, Eur. Journal of Biochemistry, *Thrombin Specificity*, vol. 151, 1985, pp. 217-224.

Torres et al, Adv. Expt. Med. Biology, *Isolation and Amino Acid Sequence of Some Thrombin*, vol. 79, 1977, pp. 267-276.

Rucker, Methods Enzymology, *Isolation of Soluble Elastin from Copper-Deficient Chick Aorta*, vol. 82, 1982, pp. 650-657.

Rich et al, Journal of Biochemistry, *Isolation of Tropoelastin a from Lathyritic Chick Aortae*, vol. 217, 1984, pp. 581-584.

Mecham et al, Biochim. Biophys., *Intrinsic Enzyme Activity Associated with Tropoelastin*, vol. 446, 1976, pp. 215-252.

Kobayashi et al, Journal of Cellular Physiology, *Serum-Induced Vascular Smooth Muscle Cell Elastolytic Activity Through Tyrosine Kinase Intracellular Signalling*, vol. 160, 1994, pp. 121-131.

Fazio et al, Journal of Investigative Dermatology, *Cloning of Full-length Elastin cDNAs from a Human Skin fibroblast Recombinant cDNA Library: Further Oligonucleotides*, vol. 91, 1988, pp. 458-464.

Yeh et al, Collagen Re. Res., *Sequence Vaiation of Bovine Elastin mRNA due to Alternative Splicing*, vol. 7, 1987, pp. 235-247.

Heim et al, Matrix, *Alternative Splicing of Rat Tropoelastin mRNA is Tissue-Specific and Developmentally Regulated*, vol. 11, 1991, pp. 359-366.

Urry et al, Biochemical and Biophysical Research Communications, *Temperature Dependence of Length of Elastin and its Polypentapeptide*, vol. 141, No. 2, Dec. 15, 1986, pp. 749-755.

Rapaka et al, Int. Journal of Peptide Protein Research, *Synthesis of Polypeptide Models of Elastin*, vol. 21, 1983, pp. 352-363.

Sandberg et al, Biochimica et Biophysical Acta, *Tropoelastin Purification From Copper-Deficient Swin: A Simplified Method*, vol. 236, 1971, pp. 542-545.

Martin et al, Gene, *Total Synthesis and Expression in Escherichia coli of a Gene Encoding Human tropoelastin*, vol. 154, 1995, pp. 159-166.

Indik et al, Proc. Natl. A.Sci. USA, *Alternative . . . by Sequence Analysis of Cloned Genomic and Complementary DNA*, vol. 84, 1987, pp. 5680-5684.

Mecham et al, Advances in Experimental Medicine and Biology, *Proteolysis of Tropoelastin*, vol. 79, 1977, pp. 209-220.

Smith et al, Gene, *Single-step Purification of Polypeptides Expressed in Escherichia coli as Fusion with Glutathione S-transferase*, vol. 67, 1988, pp. 31-40.

European Examination Report dated Nov. 18, 2005.
Wu et al, Journal of Biological Chemistry, *Glycosaminoglycans Mediate the Coacervation of Human Tropoelastin through Dominant Charge Interactions*, vol. 274, 1999, pp. 21719-21724.
Canadian Examination Report dated Sep. 30, 2005.
Kenyon et al, Journal of Biological Chemistry, *A Novel Human cDNA with a Predicted Protein Similar to Lysyl Oxidase Maps to Chromosome 15q24-q25*, vol. 268, 1993, pp. 18435-18437.
Hamalainen et al, Genomics, *Structure of the Human Lysyl Oxidase Gene*, vol. 17, 1993, pp. 544-548.
Kim et al, Journal of Biological Chemistry, *A New Gene with Sequence and Structural Similarity to the Gene with Sequence and Structural Similarity to the Gene Encoding Human Lysyl Oxidase*, vol. 270, 1995, pp. 7176-7182.
Hernan et al, Biochemistry, *Human Hemoglobin Expression in Escherichia coli: Importance of Optimal Codon Usage*, vol. 31, 1992, pp. 8619-8628.
Sharp et al, Nucleic Acids Research, *The Codon Adaptation Index—A Measure of Directional Synonymous Codon Usage Bias and Its Potential Applications*, vol. 15, 1987, pp. 1281-1295.
Boyd et al., Matrix, *Mammalian Tropoelastin: Multiple Domains of the Protein Define an Evolutionarily Divergent Amino Acid Sequence*, vol. 11, 1991, pp. 235-241.

\* cited by examiner

```
1    GATCCATGGGTGGCGTTCCGGGTGCTATCCCGGGTGGCGTTGTATTCTACC  60
     GTACCCACCGCAAGGCCCACGATAGGGCCCACCACATAAGATGG
         S  M  G  G  V  P  G  A  I  P  G  G  V  F  Y  P

61   CAGGGCGCGGGTCTGGGTGCACTGGGCGGTGGTGCGCTGGGCCCGGGTGGTAAACCGCTGA  120
     GTCCGCGCCCAGACCCACGTGACCCGCCACCACGCGACCCGGGCCCACCATTTGGCGACT
         G  A  G  L  G  A  L  G  G  G  A  L  G  P  G  G  K  P  L  K

121  AACCGGTTCCAGGCCGGTCTGGCAGGTGCTGGTCTGGGTGCAGGTCTCCAGACCCGTCCCGG  180
     TTGGCCAAGGTCCGGCCAGACCGTCCACGACCAGACCCACGTCCAGAGGTCTGGGCAGGGCC
         P  V  P  G  G  L  A  G  A  G  L  G  A  G  L  A  F  P  A

181  CGGTTACCTTCCCGGGTGCTCTGGTTCCGGGTGGCGTTGCAGACGCAGCTGCTGCGTACA  240
     GCCAATGGAAGGGCCCACGAGACCAAGGCCCACCGCAACGTCTGCGTCGACGACGCATGT
         V  T  F  P  G  A  L  V  P  G  G  V  A  D  A  A  A  Y  K
```

*FIG. 1A*

241 AAGCGGCAAAGGCAGGTGCGGGTCTGGGCGGGTACCAGTGTTGGCGGTCTGGGTGTAT 300
    TTCGCCGTTTCCGTCCACGCCCAGACCCGCCATGGTCCACAACCGCCAGACCCACATA
     A  A  K  A  G  A  G  L  G  G  V  P  G  V  G  G  L  G  V  S

301 CTGCTGGCGCAGTTGTTCCGCAGCCGGGTGCAGGTGTAAAACCGGGCAAAGTTCCAGGTG 360
    GACGACCGCGTCAACAAGGCGTCGGCCCACGTCCACATTTTGGCCCGTTTCAAGGTCCAC
     A  G  A  V  V  P  Q  P  G  A  G  V  K  P  G  K  V  P  G  V

361 TTGGTCTGCCGGGCGTATACCCGGGTGGTGTTCTGCCGGGCGCGTTTCCCAGGTGTTG 420
    AACCAGACGGCCCGCATATGGGCCCACCACAAGACGGCCCGCGCAAAGGGTCCACAAC
     G  L  P  G  V  Y  P  G  G  V  L  P  G  A  R  F  P  G  V  G

*FIG. 1B*

```
421  GTGTACTGCCGGGGCGTTCCGACCGGTGTGCAGGTGTGTTAAACCGAAGGCACCAGGTGTAGGCG   480
     CACATGACGGCCCGCAAGGCTGGCCACGTGGCCACGTTCCGTTGGTCCACATCCGC
       V  L  P  G  V  P  T  G  A  G  V  K  P  K  A  P  G  V  G  G

481  GCGCGTTCGCGGGTATCCCGGGTGTGTTGGCCCGTTCGGTGTCCGCAGCCAGGCGTTCCGC   540
     CGGCGCAAGCGCCATAGGGCCCACACAACCGGGCAAGCCACAGGCGTCGGTCCGCAAGGCG
       A  F  A  G  I  P  G  V  G  P  F  G  G  P  Q  P  G  V  P  L

541  TGGGTTACCCGATCAAAGGCCGAAGCTTCCAGGTGGCTACGGTCTGCCGTACACCACCG   600
     ACCCAATGGGCTAGTTTCGGGCTTCGAAGGTCCACCGATGCCAGACGGCATGTGGTGGC
       G  Y  P  I  K  A  P  K  L  P  G  G  Y  G  L  P  Y  T  T  G

601  GTAAACTGCCGTACGGCTACGGGTGCCGGGTGGCGTAGCAGGTGCTGCGGGTAAAGCAGGCT   660
     CATTTGACGGCATGCCGATGCCAGGCCCACCGCATCGTCCACGACGCCCATTCGTCCGA
       K  L  P  Y  G  Y  G  P  G  G  V  A  G  A  A  G  K  A  G  Y
```

*FIG. 1C*

661 ACCCAACCGGTACTGGTGTTGGTCCGCAGGCTGCTGCGGCAGCTGCGGGAAGGCAGCAG 720
    TGGGTTGGCCATGACCACAACCAGGCGTCCGACGACGCCGTCGACGCCGCTTCCGTCGTC

P  T  G  T  G  V  G  P  Q  A  A  A  A  A  A  K  A  A  A

721 CAAAATTCGGCGCGGGGTGCAGCGGGTGTTCTGCCGGGCGTAGGTGGTGCTGGCGTTCCGG 780
    GTTTTAAGCCGCGCCCCACGTCGCCCACAAGACGGCCCGCATCCACCACGACCGCAAGGCC

K  F  G  A  G  A  G  V  L  P  G  V  G  G  A  G  V  P  G

781 GTGTTCCAGGTGCGATCCCGGGCATCGGTGGTATCGCAGGCGGTAGGTACTCCGGCGGCCG 840
    CACAAGGTCCACGCTAGGGCCCGTAGCCACCATAGCGTCCGCATCCATGAGGCCGCCGGC

V  P  G  A  I  P  G  I  G  G  I  A  G  V  G  T  P  A  A  A

841 CTGCGGCTGCGCGGCAGCTGCGGCGAAAGCAGCTAAATACGGTGCGGCAGCAGGCCTGGTTC 900
    GACGCCGACGCGCCGTCGACGCCGCTTTCGTCGATTTATGCCACGCCGTCGTCCGGACCAAG

```
901   CGGGTGGTCCAGGCTTCGGTCCGGGTGTTGTAGGCGTTCCGGGTGCTGGTGTTCCGGGCG      960
      GCCCACCAGGTCCGAAGCCAGGCCCACACATCCGCAAGGCCCACGACCACAAGGCCCGC
       G  G  P  G  F  G  P  G  V  V  G  V  P  G  A  G  V  P  G  V

961   TAGGTGTTCCAGGTGCGGGCATCCCGGTTGTACCGGGTGCAGGTATCCCGGGCGCTGCGG     1020
      ATCCACAAGGTCCACGCCCGTAGGGCCAACATGGCCCACGTCCATAGGGCCCGCGACGCC
       G  V  P  G  A  G  I  P  V  V  P  G  A  G  I  P  G  A  A  V

1021  TTCCAGGTGTTGTATCCCCGGAAGCGGCAGCTAAGGCTGCTGCGAAAGCTGCGACGCTTTATGC     1080
      AAGGTCCACAACATAGGGGCCTTCGCCGTCGATTCCGACGACGCTTTCGACGCTGCGAAATACG
       P  G  V  V  S  P  E  A  A  A  K  A  A  K  A  A  A  K  Y  G

1081  GAGCTCGTCCGGGCGTTGGTGTTGGTGGCATCCCGACCTACGGTGTAGGTGCAGGCGGTT     1140
      CTCGAGCAGGCCCGCAACCACAACCACCGTAGGGCTGGATGCCACATCCACGTCCGCCAA
       A  R  P  G  V  G  V  G  G  I  P  T  Y  G  V  G  A  G  G  F
```

*FIG. 1E*

```
1141  TCCCAGGTTTCGGCGTTGGTGTTGGTGGCATCCCCGGTGTAGCTGGTGTTCCGTCTGTTG    1200
      AGGGTCCAAAGCCGCAACCACACCGTAGGGCCACATCGACCACAAGGCAGACAAC
       P   G   F   G   V   G   G   I   P   G   V   A   G   V   P   S   V   G

1201  GTGGCGTACCGGGTGTTGGTGGCGTTCCAGTGTAGGTGCGTTCCCGGAAGGCCAGGCAG    1260
      CACCGCATGGCCCACAACACCGCAAGGTCCACATCCATAGAGGGGCCTTCGCGTCCGTC
       G   V   P   G   V   G   G   V   P   G   V   G   I   S   P   E   A   Q   A   A

1261  CTGCGGGCAGCTAAAGCAGCTAGTACCTCCGGCGGCAGCAGCTGCTAAAG           1320
      GACGCCGTCGATTTCGTCGATCATGGCCAACCATGAGGCCGCCGCTCGTCGACGATTTC
       A   A   A   K   A   A   K   Y   G   V   G   T   P   A   A   A   A   K   A

1321  CAGCGGGCTAAAGCAGCTAGTTCCGGGCGTAGTGTTGCGCCAGGTGTTG            1380
      GTCGCCCGATTTCGTCGATCAAGCCTGATCAAGCCCGCATCCACAACGGGTCCACAAC
       A   A   K   A   A   Q   F   G   L   V   P   G   V   G   V   A   P   G   V   G
```

*FIG. 1F*

```
1381  GCGTAGCACCGGGTGTTGGTGTTCCGGGCGTAGGTCTGCTTGGCACCGGGTGTTGGCGTTG  1440
      CGCATCGTGGCCCACAACACAAGGAGCCCGCATCCAGACCGTGGCCCACAACCGGCAAC
           V  A  P  G  V  G  L  A  P  G  V  G  V  A

1441  CACCAGGTGTAGGTGTTGCGCCCGGGCGTTGGTGTAGCACCGGTATCGGTTCCGGGTGGCG  1500
      GTGGTCCACATCCACAACGCGGGCCCGCAACCACATCGTGGCCATAGCCAGGCCCACCGC
        P  G  V  G  V  A  P  G  V  G  V  A  P  G  I  G  P  G  G  V

1501  TTGCGGGCTGCTGCGAAATCTGCTGCGGAAGGTTGCTGCGAAGCGCAGCTGCGTGCAGCAG  1560
      AACGCCCGACGACGCTTTAGACGACGCCTTCCAACGACGCTTCGCGTCGACGCACGTCGTC
        A  A  A  K  S  A  A  K  V  A  A  K  A  Q  L  R  A  A  A

1561  CTGGTCTGGGTGCGGGCATCCCAGGTCTGGGTGTAGGTGTTGGTGTTCCGGGCCTGGGTG  1620
      GACCAGACCCACGCCCGTAGGGTCCAGACCCACATCCACAACCACAAGGCCCGGACCCAC
        G  L  G  A  G  I  P  G  L  G  V  G  V  G  V  P  G  L  G  V
```

FIG. 1G

1621 TAGGTGCAGGGGTACCGGGCTGGGTGTTGGTGCAGGCGTTCCGGGTTGCTGGCG 1680
     ATCCACGTCCCCATGGCCCGGACCCACAACCACGTCCGCAAGCCCAAAGCCACGACCGC
     G  A  G  V  P  G  L  G  V  G  A  G  V  P  G  F  G  A  G  A

1681 CGGACGAAGGTGTACGTCTGTTCCCTGTCTCCAGAACTGCGTGAAGGTGACCCGTCCTCTT 1740
     GCCTGCTTCCACATGCAGCAGGACAGAGGTCTTGACGCACTTCCACTGGGCAGGAGAA
     D  E  G  V  R  R  S  L  S  P  E  L  R  E  G  D  P  S  S

1741 CCCAGCACCTGCCGTCTACCCCGTCTCCTCCACGTGTTCCGGGCGCGTGCTGCTGA 1800
     GGGTCGTGGACGGCAGATGGGGCAGGAGGAGGTGCACAAGGCCCGCGACGACGCT
     Q  H  L  P  S  T  P  S  S  P  R  V  P  G  A  L  A  A  A  K

1801 AAGCGGGGAAATACGGTGCAGCGGGTTCCGGGTGTACTGGGGCGGGTCTGGGTGCTCTGGGGCG 1860
     TTCGCCGCTTTATGCCACGTCGCCAAGGCCCACATGACCCCGCCCAGAGACCCGC
     A  A  K  Y  G  A  A  V  P  G  V  L  G  G  L  G  A  L  G  G

FIG. 1H

```
1861  GTGTTGGTATCCCGGGCGGTGTTGTAGGTGCAGGCCCAGCTGCAGTCTGCTGCGGCAA   1920
      CACAACCATAGGGCCCGCCACAACATCCACGTCCGGGTCGACGTCGACGACGCCGTT
        V  G  I  P  G  G  V  V  G  A  G  P  A  A  A  A  A  A  K

1921  AGGCAGCGGCGAAAGCAGCTCAGTTCGGTCTGGTTGGTGCAGCAGGTCTGGGCGGTCTGG   1980
      TCCGTCGCCGCTTTCGTCGAGTCAAGCCAGACCAACCACGTCGTCCAGACCCGCCAGACC
        A  A  A  K  A  A  Q  F  G  L  V  G  A  A  G  L  G  G  L  G

1981  GTGTTGGCGGTCTGGGGTGTACCGGGCGGCGTTGGTGGTCTGGGTGGCATCCCGCCGGCGG   2040
      CACAACCGCCAGACCCCACATGGCCCGCCGCAACCACCAGACCCACCGTAGGGCGGCCGCC
        V  G  G  L  G  V  P  G  V  G  G  L  G  G  I  P  P  A  A  A

2041  CAGCTAAAGCGGCTAAATACGGTGCAGCAGGTCTGGGCGGCGTTCTGGGTGGTGCTGGTC   2100
      GTCGATTTCGCCGATTTATGCCACGTCGTCCAGACCCGCCGCAAGACCCACCACGACCAG
        A  K  A  A  K  Y  G  A  A  G  L  G  G  V  L  G  G  A  G  Q
```

*FIG. 1I*

```
2101  AGTTCCCACTGGGCGGTGTAGCGGCACGTCCGGGTTTCGTCTGTCCCCGATCTTCCCAG  2160
      TCAAGGGTGACCCGCCACATCGCCGTGCAGGCCCAAAGCCAGACAGGGCTAGAAGGGTC
       F  P  L  G  G  V  A  A  R  P  G  F  G  L  S  P  I  F  P  G

2161  GCGGTGCATGCCTGGGTAAAGCTTGCGGCCGTAAACGTAAATAATGATAG            2210
      CGCCACGTACGGACCCATTTCGAACGCCGGCATTTGCATTTATTACTATCCTAG
       G  A  C  L  G  K  A  C  G  R  K  R  K  *  *  *
```

FIG. 1J

```
  1 GGVPGAIPGGVPGGVFYPGAGLGALGGGALGPGGKPLKPVPGGLAGAGLG  50
    ||||||||||||||||||||||||||||||||||||||||||||||||||
  1 GGVPGAIPGGVPGGVFYPGAGLGALGGGALGPGGKPLKPVPGGLAGAGLG  50

51 AGLGAFPAVTFPGALVPGGVADAAAAYKAAKAGAGLGGVPGVGGLGVSAG 100
    ||||||||||||||||||||||||||||||||||||||||||||||||||
 51 AGLGAFPAVTFPGALVPGGVADAAAAYKAAKAGAGLGGVPGVGGLGVSAG 100

101 AVVPQPGAGVKPGKVPGVGLPGVYPGGVLPGARFPGVGVLPGVPTGAGVK 150
    ||||||||||||||||||||||||||||||||||||||||||||||||||
101 AVVPQPGAGVKPGKVPGVGLPGVYPGGVLPGARFPGVGVLPGVPTGAGVK 150

151 PKAPGVGGAFAGIPGVGPFGGPQPGVPLGYPIKAPKLPGGYGLPYTTGKL 200
    ||||||||||||||||||||||||||||||||||||||||||||||||||
151 PKAPGVGGAFAGIPGVGPFGGPQPGVPLGYPIKAPKLPGGYGLPYTTGKL 200

201 PYGYGPGGVAGAAGKAGYPTGTGVGPQAAAAAAAKAAAKFGAGAAGVLPG 250
    ||||||||||||||||||||||||||||||||||||||||||||||||||
201 PYGYGPGGVAGAAGKAGYPTGTGVGPQAAAAAAAKAAAKFGAGAAGVLPG 250

251 VGGAGVPGVPGAIPGIGGIAGVGTPAAAAAAAAAKAAKYGAAAGLVPGG  300
    ||||||||||||||||||||||||||||||||||||||||||||||||||
251 VGGAGVPGVPGAIPGIGGIAGVGTPAAAAAAAAAKAAKYGAAAGLVPGG  300

301 PGFGPGVVGVPGAGVPGVGVPGAGIPVVPGAGIPGAAVPGVVSPEAAAKA 350
    ||||||||||||||||||||||||||||||||||||||||||||||||||
301 PGFGPGVVGVPGAGVPGVGVPGAGIPVVPGAGIPGAAVPGVVSPEAAAKA 350

351 AAKAAKYGARPGVGVGGIPTYGVGAGGFPGFGVGVGGIPGVAGVPSVGGV 400
    ||||||||||||||||||||||||||||||||||||||||||||||||||
351 AAKAAKYGARPGVGVGGIPTYGVGAGGFPGFGVGVGGIPGVAGVPSVGGV 400
```

FIG. 2A

```
401 PGVGGVPGVGISPEAQAAAAAKAAKYGVGTPAAAAAKAAAKAAQFGLVPG 450
    |||||||||||||||||||||||||||||||||||||||||||||||||
401 PGVGGVPGVGISPEAQAAAAAKAAKYGVGTPAAAAAKAAAKAAQFGLVPG 450

451 VGVAPGVGVAPGVGVAPGVGLAPGVGVAPGVGVAPGVGVAPGIGPGGVAA 500
    |||||||||||||||||||||||||||||||||||||||||||||||||
451 VGVAPGVGVAPGVGVAPGVGLAPGVGVAPGVGVAPGVGVAPGIGPGGVAA 500

501 AAKSAAKVAAKAQLRAAAGLGAGIPGLGVGVGVPGLGVGAGVPGLGVGAG 550
    |||||||||||||||||||||||||||||||||||||||||||||||||
501 AAKSAAKVAAKAQLRAAAGLGAGIPGLGVGVGVPGLGVGAGVPGLGVGAG 550

551 VPGFGAGADEGVRRSLSPELREGDPSSSQHLPSTPSSPRVPGALAAAKAA 600
    ||||||                                  ||||||||||
551 VPGFGA..............................VPGALAAAKAA 567

601 KYGAAVPGVLGGLGALGGVGIPGGVVGAGPAAAAAAAKAAAKAAQFGLVG 650
    |||||||||||||||||||||||||||||||||||||||||||||||||
568 KYGAAVPGVLGGLGALGGVGIPGGVVGAGPAAAAAAAKAAAKAAQFGLVG 617

651 AAGLGGLGVGGLGVPGVGGLGGIPPAAAAKAAKYGAAGLGGVLGGAGQFP 700
    |||||||||||||||||||||||||||||||||||||||||||||||||
618 AAGLGGLGVGGLGVPGVGGLGGIPPAAAAKAAKYGAAGLGGVLGGAGQFP 667

701 LGGVAARPGFGLSPIFPGGACLGKACGRKRK 731
    ||||||||||||||||||||||||||||||
668 LGGVAARPGFGLSPIFPGGACLGKACGRKRK 698
```

FIG. 2B

```
  1 ATGGGTGGCGTTCCGGGTGCTGTTCCGGGTGGCGTTCCGGGTGGTGTATT  50
    ||||||||||||||||||||||||||||||||||||||||||||||||||
  1 MetGlyGlyValProGlyAlaValProGlyGlyValProGlyGlyValPh  17

51 CTACCCAGGCGCGGGTTTCGGTGCTGTTCCGGGTGGCGTTGCAGACGCAG 100
    ||||||||||||||||||||||||||||||||||||||||||||||||||
 18 eTyrProGlyAlaGlyPheGlyAlaValProGlyGlyValAlaAspAlaA  34

101 CTGCTGCGTACAAAGCGGCAAAGGCAGGTGCGGGTCTGGGCGGGGTACCA 150
    ||||||||||||||||||||||||||||||||||||||||||||||||||
 35 laAlaAlaTyrLysAlaAlaLysAlaGlyAlaGlyLeuGlyGlyValPro  50

151 GGTGTTGGCGGTCTGGGTGTATCTGCTGGCGCAGTTGTTCCGCAGCCGGG 200
    ||||||||||||||||||||||||||||||||||||||||||||||||||
 51 GlyValGlyGlyLeuGlyValSerAlaGlyAlaValValProGlnProGl  67

201 TGCAGGTGTAAAACCGGGCAAAGTTCCAGGTGTTGGTCTGCCGGGCGTAT 250
    ||||||||||||||||||||||||||||||||||||||||||||||||||
 68 yAlaGlyValLysProGlyLysValProGlyValGlyLeuProGlyValT  84

251 ACCCGGGTTTCGGTGCTGTTCCGGGCGCGCGTTTCCCAGGTGTTGGTGTA 300
    ||||||||||||||||||||||||||||||||||||||||||||||||||
 85 yrProGlyPheGlyAlaValProGlyAlaArgPheProGlyValGlyVal 100

301 CTGCCGGGCGTTCCGACCGGTGCAGGTGTTAAACCGAAGGCACCAGGTGT 350
    ||||||||||||||||||||||||||||||||||||||||||||||||||
101 LeuProGlyValProThrGlyAlaGlyValLysProLysAlaProGlyVa 117

351 AGGCGGCGCGTTCGCGGGTATCCCGGGTGTTGGCCCGTTCGGTGGTCCGC 400
    ||||||||||||||||||||||||||||||||||||||||||||||||||
118 lGlyGlyAlaPheAlaGlyIleProGlyValGlyProPheGlyGlyProG 134
```

FIG. 3A

```
401 AGCCAGGCGTTCCGCTGGGTTACCCGATCAAAGCGCCGAAGCTTCCAGGT 450
    ||||||||||||||||||||||||||||||||||||||||||||||||||
135 lnProGlyValProLeuGlyTyrProIleLysAlaProLysLeuProGly 150

451 GGCTACGGTCTGCCGTACACCACCGGTAAACTGCCGTACGGCTACGGTCC 500
    ||||||||||||||||||||||||||||||||||||||||||||||||||
151 GlyTyrGlyLeuProTyrThrThrGlyLysLeuProTyrGlyTyrGlyPr 167

501 GGGTGGCGTAGCAGGTGCTGCGGGTAAAGCAGGCTACCCAACCGGTACTG 550
    ||||||||||||||||||||||||||||||||||||||||||||||||||
168 oGlyGlyValAlaGlyAlaAlaGlyLysAlaGlyTyrProThrGlyThrG 184

551 GTGTTGGTCCGCAGGCTGCTGCGGCAGCTGCGGCGAAGGCAGCAGCAAAA 600
    ||||||||||||||||||||||||||||||||||||||||||||||||||
185 lyValGlyProGlnAlaAlaAlaAlaAlaAlaAlaLysAlaAlaAlaLys 200

601 TTCGGCGCGGGTGCAGCGGGTTTCGGTGCTGTTCCGGGCGTAGGTGGTGC 650
    ||||||||||||||||||||||||||||||||||||||||||||||||||
201 PheGlyAlaGlyAlaAlaGlyPheGlyAlaValProGlyValGlyGlyAl 217

651 TGGCGTTCCGGGTGTTCCAGGTGCGATCCCGGGCATCGGTGGTATCGCAG 700
    ||||||||||||||||||||||||||||||||||||||||||||||||||
218 aGlyValProGlyValProGlyAlaIleProGlyIleGlyGlyIleAlaG 234

701 GCGTAGGTACTCCGGCGGCCGCTGCGGCTGCGGCAGCTGCGGCGAAAGCA 750
    ||||||||||||||||||||||||||||||||||||||||||||||||||
235 lyValGlyThrProAlaAlaAlaAlaAlaAlaAlaAlaAlaAlaLysAla 250
```

*FIG. 3B*

```
 751 GCTAAATACGGTGCGGCAGCAGGCCTGGTTCCGGGTGGTCCAGGCTTCGG  800
     ||||||||||||||||||||||||||||||||||||||||||||||||||
 251 AlaLysTyrGlyAlaAlaAlaGlyLeuValProGlyGlyProGlyPheGl  267

801 TCCGGGTGTTGTAGGCGTTCCGGGTTTCGGTGCTGTTCCGGGCGTAGGTG  850
     ||||||||||||||||||||||||||||||||||||||||||||||||||
 268 yProGlyValValGlyValProGlyPheGlyAlaValProGlyValGlyV  284

851 TTCCAGGTGCGGGCATCCCGGTTGTACCGGGTGCAGGTATCCCGGGCGCT  900
     ||||||||||||||||||||||||||||||||||||||||||||||||||
 285 alProGlyAlaGlyIleProValValProGlyAlaGlyIleProGlyAla  300

901 GCGGGTTTCGGTGCTGTATCCCCGGAAGCGGCAGCTAAGGCTGCTGCGAA  950
     ||||||||||||||||||||||||||||||||||||||||||||||||||
 301 AlaGlyPheGlyAlaValSerProGluAlaAlaAlaLysAlaAlaAlaLy  317

951 AGCTGCGAAATACGGAGCTCGTCCGGGCGTTGGTGTTGGTGGCATCCCGA  1000
     ||||||||||||||||||||||||||||||||||||||||||||||||||
 318 sAlaAlaLysTyrGlyAlaArgProGlyValGlyValGlyGlyIleProT  334

1001 CCTACGGTGTAGGTGCAGGCGGTTTCCCAGGTTTCGGCGTTGGTGTTGGT  1050
     ||||||||||||||||||||||||||||||||||||||||||||||||||
 335 hrTyrGlyValGlyAlaGlyGlyPheProGlyPheGlyValGlyValGly  350

1051 GGCATCCCGGGTGTAGCTGGTGTTCCGTCTGTTGGTGGCGTACCGGGTGT  1100
     ||||||||||||||||||||||||||||||||||||||||||||||||||
 351 GlyIleProGlyValAlaGlyValProSerValGlyGlyValProGlyVa  367

1101 TGGTGGCGTTCCAGGTGTAGGTATCTCCCCGGAAGCGCAGGCAGCTGCGG  1150
     ||||||||||||||||||||||||||||||||||||||||||||||||||
 368 lGlyGlyValProGlyValGlyIleSerProGluAlaGlnAlaAlaAlaA  384
```

FIG. 3C

```
1151 CAGCTAAAGCAGCGAAGTACGGCGTTGGTACTCCGGCGGCAGCAGCTGCT 1200
     ||||||||||||||||||||||||||||||||||||||||||||||||||
 385 laAlaLysAlaAlaLysTyrGlyValGlyThrProAlaAlaAlaAlaAla 400

1201 AAAGCAGCGGCTAAAGCAGCGCAGTTCGGACTAGTTCCGGGCGTAGGTGT 1250
     ||||||||||||||||||||||||||||||||||||||||||||||||||
 401 LysAlaAlaAlaLysAlaAlaGlnPheGlyLeuValProGlyValGlyVa 417

1251 TGCGCCAGGTGTTGGCGTAGCACCGGGTGTTGGTGTTGCTCCGGGCGTAG 1300
     ||||||||||||||||||||||||||||||||||||||||||||||||||
 418 lAlaProGlyValGlyValAlaProGlyValGlyValAlaProGlyValG 434

1301 GTCTGGCACCGGGTGTTGGCGTTGCACCAGGTGTAGGTGTTGCGCCGGGC 1350
     ||||||||||||||||||||||||||||||||||||||||||||||||||
 435 lyLeuAlaProGlyValGlyValAlaProGlyValGlyValAlaProGly 450

1351 GTTGGTGTAGCACCGGGTATCGGTCCGGGTGGCGTTGCGGCTGCTGCGAA 1400
     ||||||||||||||||||||||||||||||||||||||||||||||||||
 451 ValGlyValAlaProGlyIleGlyProGlyGlyValAlaAlaAlaAlaLy 467

1401 ATCTGCTGCGAAGGTTGCTGCGAAAGCGCAGCTGCGTGCAGCAGCTGGTC 1450
     ||||||||||||||||||||||||||||||||||||||||||||||||||
 468 sSerAlaAlaLysValAlaAlaLysAlaGlnLeuArgAlaAlaAlaGlyL 484

1451 TGGGTGCGGGCATCCCAGGTCTGGGTGTAGGTGTTGGTGTTCCGGGCCTG 1500
     ||||||||||||||||||||||||||||||||||||||||||||||||||
 485 euGlyAlaGlyIleProGlyLeuGlyValGlyValGlyValProGlyLeu 500
```

FIG. 3D

```
1501 GGTGTAGGTGCAGGGGTACCGGGCCTGGGTGTTGGTGCAGGCGTTCCGGG 1550
     |||||||||||||||||||||||||||||||||||||||||||||||||
 501 GlyValGlyAlaGlyValProGlyLeuGlyValGlyAlaGlyValProGl 517

1551 TTTCGGTGCTGTTCCGGGCGCGCTGGCTGCTGCGAAAGCGGCGAAATACG 1600
     |||||||||||||||||||||||||||||||||||||||||||||||||
 518 yPheGlyAlaValProGlyAlaLeuAlaAlaAlaLysAlaAlaLysTyrG 534

1601 GTGCTGTTCCGGGTGTACTGGGCGGTCTGGGTGCTCTGGGCGGTGTTGGT 1650
     |||||||||||||||||||||||||||||||||||||||||||||||||
 535 lyAlaValProGlyValLeuGlyGlyLeuGlyAlaLeuGlyGlyValGly 550

1651 ATCCCGGGCGGTGTTGTAGGTGCAGGCCCAGCTGCAGCTGCTGCTGCGGC 1700
     |||||||||||||||||||||||||||||||||||||||||||||||||
 551 IleProGlyGlyValValGlyAlaGlyProAlaAlaAlaAlaAlaAlaAl 567

1701 AAAGGCAGCGGCGAAAGCAGCTCAGTTCGGTCTGGTTGGTGCAGCAGGTC 1750
     |||||||||||||||||||||||||||||||||||||||||||||||||
 568 aLysAlaAlaAlaLysAlaAlaGlnPheGlyLeuValGlyAlaAlaGlyL 584

1751 TGGGCGGTCTGGGTGTTGGCGGTCTGGGTGTACCGGGCGTTGGTGGTCTG 1800
     |||||||||||||||||||||||||||||||||||||||||||||||||
 585 euGlyGlyLeuGlyValGlyGlyLeuGlyValProGlyValGlyGlyLeu 600

1801 GGTGGCATCCCGCCGGCGGCGGCAGCTAAAGCGGCTAAATACGGTGCAGC 1850
     |||||||||||||||||||||||||||||||||||||||||||||||||
 601 GlyGlyIleProProAlaAlaAlaAlaLysAlaAlaLysTyrGlyAlaAl 617

1851 AGGTCTGGGTGGCGTTCTGGGTGGTGCTGGTCAGTTCCCACTGGGCGGTG 1900
     |||||||||||||||||||||||||||||||||||||||||||||||||
 618 aGlyLeuGlyGlyValLeuGlyGlyAlaGlyGlnPheProLeuGlyGlyV 634
```

FIG. 3E

```
1901 TAGCGGCACGTCCGGGTTTCGGTCTGTCCCCGATCTTCCCAGGCGGTGCA 1950
     ||||||||||||||||||||||||||||||||||||||||||||||||||
 635 alAlaAlaArgProGlyPheGlyLeuSerProIlePheProGlyGlyAla 650

1951 TGCCTGGGTAAAGCTTGCGGCCGTAAACGTAAA 1983
     |||||||||||||||||||||||||||||||||
 651 CysLeuGlyLysAlaCysGlyArgLysArgLys 661
```

FIG. 3F

```
  1 ATGGGTGGCGTTCCGGGTGCTGTTCCGGGTGGCGTTCCGGGTGGTGTATT  50
    ||||||||||||||||||||| | ||||||||||||||||||||||||||
  1 ATGGGTGGCGTTCCGGGTGCTATCCCGGGTGGCGTTCCGGGTGGTGTATT  50

51 CTACCCAGGCGCGGGTTTCGGTGC..........................  74
    ||||||||||||||||||| | |||||
 51 CTACCCAGGCGCGGGTCTGGGTGCACTGGGCGGTGGTGCGCTGGGCCCGG 100

75 ...............................................TGT  77
                                                    | |
151 GGTGCAGGTCTGGGCGCGTTCCCGGCGGTTACCTTCCCGGGTGCTCTGGT 200

78 TCCGGGTGGCGTTGCAGACGCAGCTGCTGCGTACAAAGCGGCAAAGGCAG 127
    ||||||||||||||||||||||||||||||||||||||||||||||||||
201 TCCGGGTGGCGTTGCAGACGCAGCTGCTGCGTACAAAGCGGCAAAGGCAG 250

128 GTGCGGGTCTGGGCGGGGTACCAGGTGTTGGCGGTCTGGGTGTATCTGCT 177
    ||||||||||||||||||||||||||||||||||||||||||||||||||
251 GTGCGGGTCTGGGCGGGGTACCAGGTGTTGGCGGTCTGGGTGTATCTGCT 300

178 GGCGCAGTTGTTCCGCAGCCGGGTGCAGGTGTAAAACCGGGCAAAGTTCC 227
    ||||||||||||||||||||||||||||||||||||||||||||||||||
301 GGCGCAGTTGTTCCGCAGCCGGGTGCAGGTGTAAAACCGGGCAAAGTTCC 350

228 AGGTGTTGGTCTGCCGGGCGTATACCCGGGTTTCGGTGCTGTTCCGGGCG 277
    |||||||||||||||||||||||||||||||    |||| | | |||||||
351 AGGTGTTGGTCTGCCGGGCGTATACCCGGGT...GGTGTTCTGCCGGGCG 397
```

FIG. 4A

```
278 CGCGTTTCCCAGGTGTTGGTGTACTGCCGGGCGTTCCGACCGGTGCAGGT 327
    ||||||||||||||||||||||||||||||||||||||||||||||||||
398 CGCGTTTCCCAGGTGTTGGTGTACTGCCGGGCGTTCCGACCGGTGCAGGT 447

328 GTTAAACCGAAGGCACCAGGTGTAGGCGGCGCGTTCGCGGGTATCCCGGG 377
    ||||||||||||||||||||||||||||||||||||||||||||||||||
448 GTTAAACCGAAGGCACCAGGTGTAGGCGGCGCGTTCGCGGGTATCCCGGG 497

378 TGTTGGCCCGTTCGGTGGTCCGCAGCCAGGCGTTCCGCTGGGTTACCCGA 427
    ||||||||||||||||||||||||||||||||||||||||||||||||||
498 TGTTGGCCCGTTCGGTGGTCCGCAGCCAGGCGTTCCGCTGGGTTACCCGA 547

428 TCAAAGCGCCGAAGCTTCCAGGTGGCTACGGTCTGCCGTACACCACCGGT 477
    ||||||||||||||||||||||||||||||||||||||||||||||||||
548 TCAAAGCGCCGAAGCTTCCAGGTGGCTACGGTCTGCCGTACACCACCGGT 597

478 AAACTGCCGTACGGCTACGGTCCGGGTGGCGTAGCAGGTGCTGCGGGTAA 527
    ||||||||||||||||||||||||||||||||||||||||||||||||||
598 AAACTGCCGTACGGCTACGGTCCGGGTGGCGTAGCAGGTGCTGCGGGTAA 647

528 AGCAGGCTACCCAACCGGTACTGGTGTTGGTCCGCAGGCTGCTGCGGCAG 577
    ||||||||||||||||||||||||||||||||||||||||||||||||||
648 AGCAGGCTACCCAACCGGTACTGGTGTTGGTCCGCAGGCTGCTGCGGCAG 697

578 CTGCGGCGAAGGCAGCAGCAAAATTCGGCGCGGGTGCAGCGGGTTTCGGT 627
    |||||||||||||||||||||||||||||||||||||||||      |||
698 CTGCGGCGAAGGCAGCAGCAAAATTCGGCGCGGGTGCAGCG......GGT 741

628 GCTGTTCCGGGCGTAGGTGGTGCTGGCGTTCCGGGTGTTCCAGGTGCGAT 677
    |  |  ||||||||||||||||||||||||||||||||||||||||||||
742 GTTCTGCCGGGCGTAGGTGGTGCTGGCGTTCCGGGTGTTCCAGGTGCGAT 791
```

FIG. 4B

```
 678 CCCGGGCATCGGTGGTATCGCAGGCGTAGGTACTCCGGCGGCCGCTGCGG  727
     ||||||||||||||||||||||||||||||||||||||||||||||||||
 792 CCCGGGCATCGGTGGTATCGCAGGCGTAGGTACTCCGGCGGCCGCTGCGG  841

728 CTGCGGCAGCTGCGGCGAAAGCAGCTAAATACGGTGCGGCAGCAGGCCTG  777
     ||||||||||||||||||||||||||||||||||||||||||||||||||
 842 CTGCGGCAGCTGCGGCGAAAGCAGCTAAATACGGTGCGGCAGCAGGCCTG  891

778 GTTCCGGGTGGTCCAGGCTTCGGTCCGGGTGTTGTAGGCGTTCCGGGTTT  827
     |||||||||||||||||||||||||||||||||||||||||||||||
 892 GTTCCGGGTGGTCCAGGCTTCGGTCCGGGTGTTGTAGGCGTTCCGGGT..  939

828 CGGTGCTGTTCCGGGCGTAGGTGTTCCAGGTGCGGGCATCCCGGTTGTAC  877
     |  ||  |||||||||||||||||||||||||||||||||||||||||||
 940 .GCTGGTGTTCCGGGCGTAGGTGTTCCAGGTGCGGGCATCCCGGTTGTAC  988

878 CGGGTGCAGGTATCCCGGGCGCTGCGGGTTTCGGTGCTGTATCCCCGGAA  927
     |||||||||||||||||||||||||| |    ||||  ||||||||||||
 989 CGGGTGCAGGTATCCCGGGCGCTGCGGTTCCAGGTGTTGTATCCCCGGAA 1038

928 GCGGCAGCTAAGGCTGCTGCGAAAGCTGCGAAATACGGAGCTCGTCCGGG  977
     ||||||||||||||||||||||||||||||||||||||||||||||||||
1039 GCGGCAGCTAAGGCTGCTGCGAAAGCTGCGAAATACGGAGCTCGTCCGGG 1088

978 CGTTGGTGTTGGTGGCATCCCGACCTACGGTGTAGGTGCAGGCGGTTTCC 1027
     ||||||||||||||||||||||||||||||||||||||||||||||||||
1089 CGTTGGTGTTGGTGGCATCCCGACCTACGGTGTAGGTGCAGGCGGTTTCC 1138

1028 CAGGTTTCGGCGTTGGTGTTGGTGGCATCCCGGGTGTAGCTGGTGTTCCG 1077
     ||||||||||||||||||||||||||||||||||||||||||||||||||
1139 CAGGTTTCGGCGTTGGTGTTGGTGGCATCCCGGGTGTAGCTGGTGTTCCG 1188
```

FIG. 4C

```
1078 TCTGTTGGTGGCGTACCGGGTGTTGGTGGCGTTCCAGGTGTAGGTATCTC 1127
     ||||||||||||||||||||||||||||||||||||||||||||||||||
1189 TCTGTTGGTGGCGTACCGGGTGTTGGTGGCGTTCCAGGTGTAGGTATCTC 1238

1128 CCCGGAAGCGCAGGCAGCTGCGGCAGCTAAAGCAGCGAAGTACGGCGTTG 1177
     ||||||||||||||||||||||||||||||||||||||||||||||||||
1239 CCCGGAAGCGCAGGCAGCTGCGGCAGCTAAAGCAGCGAAGTACGGCGTTG 1288

1178 GTACTCCGGCGGCAGCAGCTGCTAAAGCAGCGGCTAAAGCAGCGCAGTTC 1227
     ||||||||||||||||||||||||||||||||||||||||||||||||||
1289 GTACTCCGGCGGCAGCAGCTGCTAAAGCAGCGGCTAAAGCAGCGCAGTTC 1338

1228 GGACTAGTTCCGGGCGTAGGTGTTGCGCCAGGTGTTGGCGTAGCACCGGG 1277
     ||||||||||||||||||||||||||||||||||||||||||||||||||
1339 GGACTAGTTCCGGGCGTAGGTGTTGCGCCAGGTGTTGGCGTAGCACCGGG 1388

1278 TGTTGGTGTTGCTCCGGGCGTAGGTCTGGCACCGGGTGTTGGCGTTGCAC 1327
     ||||||||||||||||||||||||||||||||||||||||||||||||||
1389 TGTTGGTGTTGCTCCGGGCGTAGGTCTGGCACCGGGTGTTGGCGTTGCAC 1438

1328 CAGGTGTAGGTGTTGCGCCGGGCGTTGGTGTAGCACCGGGTATCGGTCCG 1377
     ||||||||||||||||||||||||||||||||||||||||||||||||||
1439 CAGGTGTAGGTGTTGCGCCGGGCGTTGGTGTAGCACCGGGTATCGGTCCG 1488

1378 GGTGGCGTTGCGGCTGCTGCGAAATCTGCTGCGAAGGTTGCTGCGAAAGC 1427
     ||||||||||||||||||||||||||||||||||||||||||||||||||
1489 GGTGGCGTTGCGGCTGCTGCGAAATCTGCTGCGAAGGTTGCTGCGAAAGC 1538
```

FIG. 4D

```
1428 GCAGCTGCGTGCAGCAGCTGGTCTGGGTGCGGGCATCCCAGGTCTGGGTG 1477
     |||||||||||||||||||||||||||||||||||||||||||||||||
1539 GCAGCTGCGTGCAGCAGCTGGTCTGGGTGCGGGCATCCCAGGTCTGGGTG 1588

1478 TAGGTGTTGGTGTTCCGGGCCTGGGTGTAGGTGCAGGGGTACCGGGCCTG 1527
     |||||||||||||||||||||||||||||||||||||||||||||||||
1589 TAGGTGTTGGTGTTCCGGGCCTGGGTGTAGGTGCAGGGGTACCGGGCCTG 1638

1528 GGTGTTGGTGCAGGCGTTCCGGGTTTCGGTGC................. 1559
     |||||||||||||||||||||||||||||||||
1639 GGTGTTGGTGCAGGCGTTCCGGGTTTCGGTGCTGGCGCGGACGAAGGTGT 1688
                                     .
                                     .
1560 ........................TGTTCCGGGCGCGCTGGCT 1578
                             |||||||||||||||||||
1739 AGCACCTGCCGTCTACCCCGTCCTCTCCACGTGTTCCGGGCGCGCTGGCT 1788

1579 GCTGCGAAAGCGGCGAAATACGGT...GCTGTTCCGGGTGTACTGGGCGG 1625
     ||||||||||||||||||||||||   || ||||||||||||||||||||
1789 GCTGCGAAAGCGGCGAAATACGGTGCAGCGGTTCCGGGTGTACTGGGCGG 1838

1626 TCTGGGTGCTCTGGGCGGTGTTGGTATCCCGGGCGGTGTTGTAGGTGCAG 1675
     |||||||||||||||||||||||||||||||||||||||||||||||||
1839 TCTGGGTGCTCTGGGCGGTGTTGGTATCCCGGGCGGTGTTGTAGGTGCAG 1888

1676 GCCCAGCTGCAGCTGCTGCTGCGGCAAAGGCAGCGGCGAAAGCAGCTCAG 1725
     |||||||||||||||||||||||||||||||||||||||||||||||||
1889 GCCCAGCTGCAGCTGCTGCTGCGGCAAAGGCAGCGGCGAAAGCAGCTCAG 1938
```

FIG. 4E

```
1726 TTCGGTCTGGTTGGTGCAGCAGGTCTGGGCGGTCTGGGTGTTGGCGGTCT 1775
     ||||||||||||||||||||||||||||||||||||||||||||||||||
1939 TTCGGTCTGGTTGGTGCAGCAGGTCTGGGCGGTCTGGGTGTTGGCGGTCT 1988

1776 GGGTGTACCGGGCGTTGGTGGTCTGGGTGGCATCCCGCCGGCGGCGGCAG 1825
     ||||||||||||||||||||||||||||||||||||||||||||||||||
1989 GGGTGTACCGGGCGTTGGTGGTCTGGGTGGCATCCCGCCGGCGGCGGCAG 2038

1826 CTAAAGCGGCTAAATACGGTGCAGCAGGTCTGGGTGGCGTTCTGGGTGGT 1875
     ||||||||||||||||||||||||||||||||||||||||||||||||||
2039 CTAAAGCGGCTAAATACGGTGCAGCAGGTCTGGGTGGCGTTCTGGGTGGT 2088

1876 GCTGGTCAGTTCCCACTGGGCGGTGTAGCGGCACGTCCGGGTTTCGGTCT 1925
     ||||||||||||||||||||||||||||||||||||||||||||||||||
2089 GCTGGTCAGTTCCCACTGGGCGGTGTAGCGGCACGTCCGGGTTTCGGTCT 2138

1926 GTCCCCGATCTTCCCAGGCGGTGCATGCCTGGGTAAAGCTTGCGGCCGTA 1975
     ||||||||||||||||||||||||||||||||||||||||||||||||||
2139 GTCCCCGATCTTCCCAGGCGGTGCATGCCTGGGTAAAGCTTGCGGCCGTA 2188

1976 AACGTAAATAATGATAG 1992
     |||||||||||||||||
2189 AACGTAAATAATGATAG 2205
```

FIG. 4F

```
                    10         20         30         40         50         60         70         80
MGGVPGAIPGGVPGGVFYPGAGLGALGGGALGPGGKPLKPVPGGLAGAGLGAGLGAFPAVTFPGALVPGGVADAAAAYKA
::  :: ::::::::::                                              :  :  ::::::::::
MGGVPGAVPGGVPGGVFY-------------------------------P----GA--G-------F-GA-VPGGVADAAAAYKA
                                                                        10         20         30

90        100        110        120        130        140        150
AKAGAGLGGVPGVGGLGVSAGAVVPQPGVGLPGYPIKAPKLPGGYGLPYTTGKLPYGYGPGGVAGAAGKAGYPTGTGVGPQAAAAAAKAAA
::::::::::::::::::::::::::::  :::::::                    ::::::::::::::::::::::::::::::::::
AKAGAGLGGVPGVGGLGVSAGAVVPQPGAGVKPGKVPGGVYPG-GVLPGARFPGVGVLPGVPTGAGVKPKAPGVGG
     50         60         70         80         90        100        110

170        180        190        200        210        220        230
AFAGIPGVGPFGGPQPGVPLGYPIKAPKLPGGYGLPYTTGKLPYGYGPGGVAGAAGKAGYPTGTGVGPQAAAAAAKAAA
::::::::::::::::::::::::::::::::::::::::::::::::::::::::::::::::::::::::::::::
AFAGIPGVGPFGGPQPGVPLGYPIKAPKLPGGYGLPYTTGKLPYGYGPGGVAGAAGKAGYPTGTGVGPQAAAAAAKAAA
    130        140        150        160        170        180        190
```

FIG. 5A

```
              250           260           270           280           290           300           310
KFGAGAA--GVLPGVGGAGVPGVPGAIPGIGGIAGVGTPAAAAAAAAKAAKYGAAAGLVPGGPGFGPGVVGVPGAG-V
::::::  :  :::::::::::::::::::::::::::::::::::::::::::::::::::::::::::::  :
KFGAGAAGFGAVPGVGGAGVPGVPGAIPGIGGIAGVGTPAAAAAAAAKAAKYGAAAGLVPGGPGFGPGVVGVPGFGAV
              210           220           230           240           250           260           270

320           330           340           350           360           370           380           390
              PGVGVPGAGIPVVPGAGIPGAAVPGVVSPEAAAKAAAKAAKYGARPGVGVGGIPTYGVGAGGFPGFGVGVGGIPGVAGVP
              ::::::::::::::::::::::::::::::::::::::::::::::::::::::::::::::::::::::::::::::
              PGVGVPGAGIPVVPGAGIPGAAGFGAVSPEAAAKAAAKAAKYGARPGVGVGGIPTYGVGAGGFPGFGVGVGGIPGVAGVP
              290           300           310           320           330           340           350
```

*FIG. 5B*

```
        400         410         420         430         440         450         460         470
SVGGVPGGVPGVGISPEAQAAAAAAKAAKYGVGTPAAAAAAKAAKAAQFGLVPGVGVAPGVGVAPGVGVAPGVGLAPGV
        370         380         390         400         410         420         430
SVGGVPGVGGVPGVGISPEAQAAAAAAKAAKYGVGTPAAAAAAKAAKAAQFGLVPGVGVAPGVGVAPGVGLAPGV 480         490         500         510         520         530         540         550
GVAPGVGVAPGIGPGGVAAAAKSAAKVAAKAQLRAAAGLGAGIPGLGVGVGVPGLGVGAGVPGLGVGAGVPGFG
        450         460         470         480         490         500         510
GVAPGVGVAPGIGPGGVAAAAKSAAKVAAKAQLRAAAGLGAGIPGLGVGVGVPGLGVGAGVPGLGVGAGVPGF- 560         570         580         590         600         610         620         630
AGADEGVRRSLSPELREGDPSSSQHLPSTPSSPRVPGALAAAKAAKYGAAVPGVLGGLGALGGVIPGGVVGAGPAAAAA
                                              VPGALAAAKAAKYG-AVPGVLGGLGALGGVIPGGVVGAGPAAAAA
-GA------                                             530         540         550         560
```

*FIG. 5C*

```
          640       650       660       670       680       690       700       710
AAKAAAKAAQFGLVGAAGLGGLGVGGLGVPGVGGLGGIPPAAAKAAKYGAAGLGGVLGGAGGQFPLGGVAARPGFGLSPI
...       ...       ...       ...       ...       ...       ...       ...       ...
AAKAAAKAAQFGLVGAAGLGGLGVGGLGVPGVGGLGGIPPAAAKAAKYGAAGLGGVLGGAGGQFPLGGVAARPGFGLSPI
          570       580       590       600       610       620       630       640

720       730
FPGGACLGKACGRKRK
...       ...
FPGGACLGKACGRKRK
650       660
```

*FIG. 5D*

```
 948 TCCGCCATGGGAGGTGTTCCGGGCGCGCTGGCTGCTGCGAAAGCGGCGAA  997
     ||||||||||||||||||||||||||||||||||||||||||||||||||
   1 SerAlaMetGlyGlyValProGlyAlaLeuAlaAlaAlaLysAlaAlaLy   17

998 ATACGGTGCAGCGGTTCCGGGTGTACTGGGCGGTCTGGGTGCTCTGGGCG 1047
     ||||||||||||||||||||||||||||||||||||||||||||||||||
  18 sTyrGlyAlaAlaValProGlyValLeuGlyGlyLeuGlyAlaLeuGlyG   34

1048 GTGTTGGTATCCCGGGCGGTGTTGTAGGTGCAGGCCCAGCTGCAGCTGCT 1097
     ||||||||||||||||||||||||||||||||||||||||||||||||||
  35 lyValGlyIleProGlyGlyValValGlyAlaGlyProAlaAlaAlaAla   50

1098 GCTGCGGCAAAGGCAGCGGCGAAAGCAGCTCAGTTCGGTCTGGTTGGTGC 1147
     ||||||||||||||||||||||||||||||||||||||||||||||||||
  51 AlaAlaAlaLysAlaAlaAlaLysAlaAlaGlnPheGlyLeuValGlyAl   67

1148 AGCAGGTCTGGGCGGTCTGGGTGTTGGCGGTCTGGGTGTACCGGGCGTTG 1197
     ||||||||||||||||||||||||||||||||||||||||||||||||||
  68 aAlaGlyLeuGlyGlyLeuGlyValGlyGlyLeuGlyValProGlyValG   84

1198 GTGGTCTGGGTGGCATCCCGCCGGCGGCGGCAGCTAAAGCGGCTAAATAC 1247
     ||||||||||||||||||||||||||||||||||||||||||||||||||
  85 lyGlyLeuGlyGlyIleProProAlaAlaAlaAlaLysAlaAlaLysTyr  100

1248 GGTGCAGCAGGTCTGGGTGGCGTTCTGGGTGGTGCTGGTCAGTTCCCACT 1297
     ||||||||||||||||||||||||||||||||||||||||||||||||||
 101 GlyAlaAlaGlyLeuGlyGlyValLeuGlyGlyAlaGlyGlnPheProLe  117

1298 GGGCGGTGTAGCGGCACGTCCGGGTTTCGGTCTGTCCCCGATCTTCCCAG 1347
     ||||||||||||||||||||||||||||||||||||||||||||||||||
 118 uGlyGlyValAlaAlaArgProGlyPheGlyLeuSerProIlePheProG  134

1348 GCGGTGCATGCCTGGGTAAAGCTTGCGGCCGTAAACGTAAA         1388
     |||||||||||||||||||||||||||||||||||||||||
 135 lyGlyAlaCysLeuGlyLysAlaCysGlyArgLysArgLys          147
```

FIG. 7

```
 948 TCCGCCATGGGAGCTCTGGTAGGCCTGGGCGTACCGGGCCTGGGTGTTGG  997
     ||||||||||||||||||||||||||||||||||||||||||||||||||
   1 SerAlaMetGlyAlaLeuValGlyLeuGlyValProGlyLeuGlyValGl  17

998 TGCAGGCGTTCCGGGTTTCGGTGCTGGCGCGGACGAAGGTGTACGTCGTT 1047
     ||||||||||||||||||||||||||||||||||||||||||||||||||
  18 yAlaGlyValProGlyPheGlyAlaGlyAlaAspGluGlyValArgArgS  34

1048 CCCTGTCTCCAGAACTGCGTGAAGGTGACCCGTCCTCTTCCCAGCACCTG 1097
     ||||||||||||||||||||||||||||||||||||||||||||||||||
  35 erLeuSerProGluLeuArgGluGlyAspProSerSerSerGlnHisLeu  50

1098 CCGTCTACCCCGTCCTCTCCACGTGTTCCGGGCGCGCTGGCTGCTGCGAA 1147
     ||||||||||||||||||||||||||||||||||||||||||||||||||
  51 ProSerThrProSerSerProArgValProGlyAlaLeuAlaAlaAlaLy  67

1148 AGCGGCGAAATACGGTGCAGCGGTTCCGGGTGTACTGGGCGGTCTGGGTG 1197
     ||||||||||||||||||||||||||||||||||||||||||||||||||
  68 sAlaAlaLysTyrGlyAlaAlaValProGlyValLeuGlyGlyLeuGlyA  84

1198 CTCTGGGCGGTGTTGGTATCCCGGGCGGTGTTGTAGGTGCAGGCCCAGCT 1247
     ||||||||||||||||||||||||||||||||||||||||||||||||||
  85 laLeuGlyGlyValGlyIleProGlyGlyValValGlyAlaGlyProAla 100
```

FIG. 8A

```
1248 GCAGCTGCTGCTGCGGCAAAGGCAGCGGCGAAAGCAGCTCAGTTCGGTCT 1297
     ||||||||||||||||||||||||||||||||||||||||||||||||||
 101 AlaAlaAlaAlaAlaAlaLysAlaAlaAlaLysAlaAlaGlnPheGlyLe 117

1298 GGTTGGTGCAGCAGGTCTGGGCGGTCTGGGTGTTGGCGGTCTGGGTGTAC 1347
     ||||||||||||||||||||||||||||||||||||||||||||||||||
 118 uValGlyAlaAlaGlyLeuGlyGlyLeuGlyValGlyGlyLeuGlyValP 134

1348 CGGGCGTTGGTGGTCTGGGTGGCATCCCGCCGGCGGCGGCAGCTAAAGCG 1397
     ||||||||||||||||||||||||||||||||||||||||||||||||||
 135 roGlyValGlyGlyLeuGlyGlyIleProProAlaAlaAlaAlaLysAla 150

1398 GCTAAATACGGTGCAGCAGGTCTGGGTGGCGTTCTGGGTGGTGCTGGTCA 1447
     ||||||||||||||||||||||||||||||||||||||||||||||||||
 151 AlaLysTyrGlyAlaAlaGlyLeuGlyGlyValLeuGlyGlyAlaGlyGl 167

1448 GTTCCCACTGGGCGGTGTAGCGGCACGTCCGGGTTTCGGTCTGTCCCCGA 1497
     ||||||||||||||||||||||||||||||||||||||||||||||||||
 168 nPheProLeuGlyGlyValAlaAlaArgProGlyPheGlyLeuSerProI 184

1498 TCTTCCCAGGCGGTGCATGCCTGGGTAAAGCTTGCGGCCGTAAACGTAAA 1547
     ||||||||||||||||||||||||||||||||||||||||||||||||||
 185 lePheProGlyGlyAlaCysLeuGlyLysAlaCysGlyArgLysArgLys 200
```

FIG. 8B

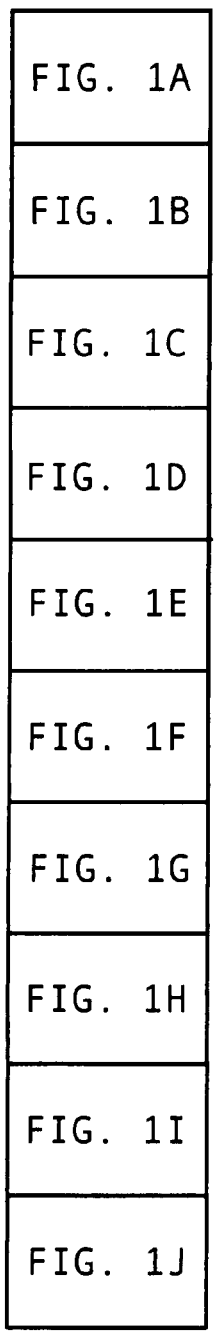
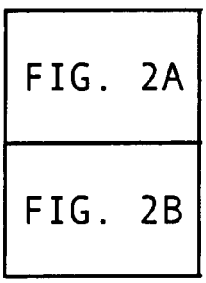
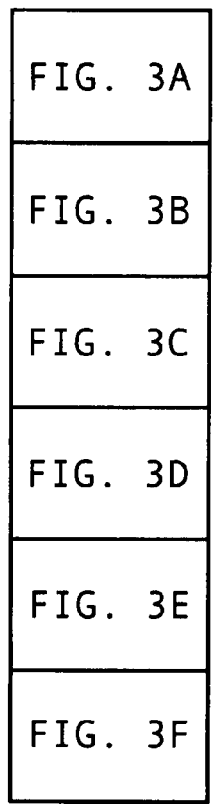
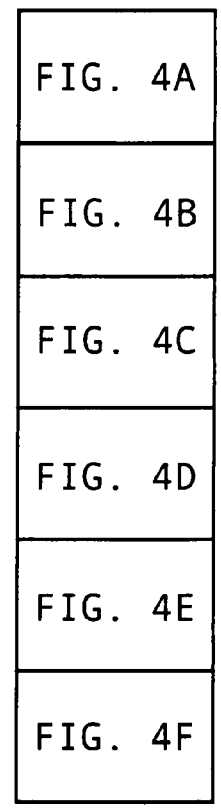
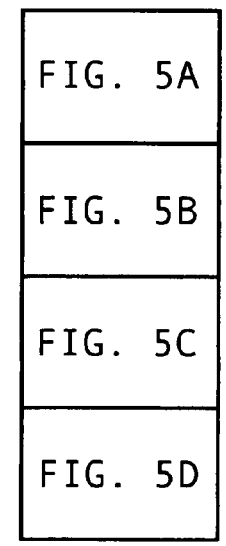
*FIG. 9*

TROPOELASTIN DERIVATIVES

The present application is a continuation of application Ser. No. 11/053,710, filed Feb. 8, 2005 (now abandoned), which is a continuation of application Ser. No. 09/463,091, filed Mar. 31, 2000 (now granted as U.S. Pat. No. 7,193,043) which, in turn, claims priority under 35 USC 371 based on PCT Application PCT/AU98/00564, filed Jul. 17, 1998.

TECHNICAL FIELD

The present invention relates to derivatives of human tropoelastin and variants thereof, to genetic constructs encoding the amino acid sequences of the derivatives and variants and to uses of the derivatives and variants. In particular, the derivatives of the present invention have elastin-like properties or macro-molecular binding properties.

BACKGROUND ART

There are various forms of tropoelastin that typically appear to consist of two types of alternating domains: those rich in hydrophobic amino acids (responsible for the elastic properties) and those rich in lysine residues (responsible for cross-link formation). Hydrophobic and cross-linking domains are encoded in separate exons (Indik et al 1987).

The 26 A region of human tropoelastin is unique amongst tropoelastin domains in that, due to the absence of lysine, this region does not participate in elastin cross-link formation. Furthermore, this region is a serine-rich domain and lacks hydrophobic stretches, indicating that it is unlikely to contribute to the elasticity of tropoelastin. There is otherwise limited information on the structure and functional relationships of the 26 A region (Bedell-Hogan et al., 1993).

The gene for tropoelastin is believed to be present as a single copy in the mammalian genome, and is expressed in the form of multiple transcripts, distinguished by alternative splicing of the pre-mRNA (Indik et al, 1990; Oliver et al, 1987). Modest expression of a natural human tropoelastin sequence has been achieved by Indik et al (1990) using cDNA, providing free polypeptide which unfortunately was unstable.

Expression of substantial amounts of human tropoelastin using synthetic polynucleotides is reported in WO94/14958. In particular, a construct, SHEL, providing substantial amounts of full length human tropoelastin is described.

DESCRIPTION OF THE INVENTION

In the specification and claims, "derivatives of human tropoelastin" or "tropoelastin derivatives" means novel peptides, polypeptides or proteins which contain amino acid sequences derived from the native amino acid sequences of human tropoelastin molecules. The amino acid sequences of the derivatives of human tropoelastin may be derived from any of the amino acid sequences of the isoforms of human tropoelastin. Derivatives of human tropoelastin are distinguished from human tropoelastin molecules in that the amino acid sequences of derivatives are altered with respect to native tropoelastin sequences by substitution, addition or deletion of residues, or a combination of these alterations, in derivative amino acid sequences.

In a first aspect, the present invention provides derivatives of human tropoelastin which have elastin-like properties. Elastin-like properties are a combination of elastic properties, including the phenomenon of recoil following molecular distention under appropriate conditions, and the ability to be cross-linked to other elastin molecules and/or other elastin-like molecules.

In a second aspect, the present invention provides derivatives of human tropoelastin which have macro-molecular binding properties including the ability to bind glycosaminoglycans.

In a third aspect, the present invention provides derivatives of human tropoelastin which have elastin-like properties and macro-molecular binding properties.

The present invention further provides amino acid sequence variants of the derivatives of the invention. In the specification and claims "variants" means amino acid sequences which retain the properties of the corresponding derivative of human tropoelastin, for example, elastin-like properties or macro-molecular binding properties, or a combination of elastin-like properties and macro-molecular binding properties, and have an amino acid sequence which is homologous with the amino acid sequence of the corresponding derivative. For the purposes of this description, "homology" between the amino acid sequence of a particular derivative of human tropoelastin and another amino acid sequence connotes a likeness short of identity, indicative of a derivation of one sequence from the other. In particular, an amino acid sequence is homologous to a derivative of human tropoelastin if the alignment of that amino acid sequence with the sequence of the derivative of human tropoelastin reveals a similarity of about 65% over any 20 amino acid stretch or over any repetitive element of the molecules shorter than 20 amino acids in length. Such a sequence comparison can be performed via known algorithms, such as that of Lipman and Pearson (1985). Similarity is observed between amino acids where those amino acids have a side chain which confers a similar chemical property in the same chemical environment. For example, threonine and serine are similar amino acids; aspartic acid and glutamic acid are similar amino acids; valine, leucine and isoleucine are similar amino acids etc. Thus, an amino acid sequence may be considered homologous with the amino acid sequence of a human tropoelastin derivative because the alignment of those sequences reveals a similarity of 65%, although at each amino acid position in the aligned sequences, none of the residues are identical.

Inasmuch as the present invention provides derivatives of human tropoelastin and amino acid sequence variants of those derivatives, the invention thus extends to amino acid sequence variants incorporating amino acid sequences of non-human tropoelastins. Amino acid sequence variants which are non-human tropoelastin derivatives, or are based all, or in part, on non-human tropoelastin derivatives retain properties of the corresponding derivative of non-human tropoelastin, for example, elastin-like properties or macro-molecular binding properties, or a combination of elastin-like properties and macro-molecular binding properties, and have an amino acid sequence which is homologous with the amino acid sequence of the corresponding human derivative. The variants of the invention also include variants of the non-human tropoelastin derivatives, or of derivatives based on the non-human tropoelastin derivatives. "Homology" between the amino acid sequence of a particular derivative of non-human tropoelastin and another amino acid sequence connotes a likeness short of identity, indicative of a derivation of one sequence from the other. In particular, an amino acid sequence is homologous to a derivative of non-human tropoelastin if the alignment of that amino acid sequence with the sequence of the derivative of non-human tropoelastin reveals a similarity of about 65% over any 20 amino acid stretch or over any repetitive element of the molecules shorter than 20 amino acids in length. The skilled addressee will understand that species that are substantially phylogenetically related to humans express tropoelastin molecules which consist of amino acid sequences with homology to human tropoelastin amino acid sequences. Indeed, amino acid sequences of non-human tropoelastins have been determined, including the amino acid sequences of chick tropoelastin, bovine tropoelastin and rat tropoelastin (Bressan et al. 1987, Raju et al. 1987, Pierce et al 1992) and over multiple regions, these are homologous with the human tropoelastin amino acid sequences. The skilled addressee will recognise therefore, that derivatives of human tropoelastin and amino acid sequence variants of those derivatives will necessarily encompass corresponding tropoelastin amino acid sequences from these and other non-human species.

The present invention provides a tropoelastin derivative comprising the amino acid sequence of SHELδmodified (SEQ ID NO:5). The amino acid sequence of SHELδmodified and the alignment of that amino acid sequence with the human tropoelastin sequence is shown in FIG. 5.

The invention also provides an amino acid sequence variant of the derivative comprising the amino acid sequence of SHELδmodified.

The invention also provides a polynucleotide encoding a tropoelastin derivative comprising the amino acid sequence of SHELδmodified. The nucleotide sequence encoding SHELδmodified is shown in FIG. 3 (SEQ ID NO: 4). Preferably the polynucleotide comprises the nucleotide sequence which corresponds to SHELδmodified shown in FIG. 3.

The invention also provides a polynucleotide encoding an amino acid sequence variant of the derivative SHELδmodified.

The present invention further provides a synthetic polynucleotide encoding a tropoelastin derivative comprising the amino acid sequence of SHELδ26A (SEQ ID NO:3). A synthetic polynucleotide is a molecule which comprises a nucleotide sequence that contains silent mutations with respect to the corresponding native polynucleotide molecule. The silent mutations enhance the expression of the synthetic polynucleotide. The amino acid sequence of SHELδ26A and the alignment of that amino acid sequence with the human tropoelastin sequence is shown in FIG. 2. The SHELδ26A derivative excludes the SHEL coding sequence corresponding to exon 26A.

Preferably the synthetic polynucleotide comprises the sequence shown in FIG. 1 (SEQ ID NO:1) from nucleotide position 1 to 1676 contiguous with nucleotide position 1775 to 2210.

The invention also provides a polynucleotide encoding an amino acid sequence variant of the derivative SHELδ26A.

The invention also provides an amino acid sequence variant of the derivative comprising the amino acid sequence of SHELδ26A.

The present inventor has, for the first time, shown that the region encoded by exon 26A (peptide 26A) of the tropoelastin gene binds glycosaminoglycans (GAGs) (FIGS. 6A and B). GAGs are macro-molecules particularly associated with the extracellular environment. These molecules play an important role in the architecture and mechanical properties of connective tissues and mediate interactions with and availability of other molecules.

Thus, the present invention provides a tropoelastin derivative comprising the amino acid sequence of peptide 26A. Peptide 26A has the amino acid sequence: GADEGVRRSL-SPELREGDPSSSQHLPSTPSSPRV (SEQ ID NO: 12) or GADEGVRRSLSPELREGDPSSSQHLPSTPSSPRF (SEQ ID NO: 13).

The present invention also provides an amino acid sequence variant of the derivative comprising the amino acid sequence of peptide 26A.

The invention also provides a polynucleotide encoding a tropoelastin derivative comprising the amino acid sequence of peptide 26A. Preferably the polynucleotide comprises the nucleotide sequence shown in FIG. 1 (SEQ ID NO: 1) from nucleotide position 1687 to 1778. Preferably the 3' terminal codon is GTT (which encodes V) or TTT (which encodes F).

The invention also provides a polynucleotide encoding an amino acid sequence variant of the derivative comprising the amino acid sequence of peptide 26A.

In appreciating the GAG binding property of peptide 26A, the present inventor envisages the generation of novel subsets of hybrid molecules, comprising biological polymers which are linked to peptide 26A, wherein the peptide 26A imparts GAG binding activity to the polymer. In particular, the present inventor has recognised that the deletion or insertion of the peptide 26A amino acid sequence, or a variant of that amino acid sequence will alter GAG binding activity. Thus, the present invention relates to tropoelastin derivatives in which full length or partial length tropoelastin molecules have been modified by the addition of one or more exon 26A regions to enhance interactions with GAGs. Moreover, the invention relates to site directed modification of the amino acid sequence of peptide 26A so as to generate variants of the peptide 26A amino acid sequence which have altered affinity or altered specificity for GAGs. Tropoelastin derivatives or variants of the derivatives which contain altered GAG binding activity may be uncross-linked or cross-linked.

In another aspect, the invention provides a hybrid molecule. In the specification and claims, "hybrid molecule" means a molecule comprising a biological polymer which is linked to a tropoelastin derivative comprising the amino acid sequence of peptide 26A or an amino acid sequence variant of a derivative comprising the amino acid sequence of peptide 26A. Preferably the biological polymer is a protein. More preferably the protein is selected from the group consisting of growth factors, cytokines and antibodies. Alternatively the biological polymer is selected from the group consisting of lipids, sugars or nucleic acids.

In one embodiment, and where the biological polymer is a protein, the hybrid molecule is produced by recombinant DNA techniques, including for example the construction of a nucleotide sequence which encodes the biological polymer and the tropoelastin derivative comprising the amino acid sequence of peptide 26A, or the amino acid sequence variant of a derivative comprising the amino acid sequence of peptide 26A, in a single open reading frame. Alternatively, the hybrid molecule may be produced synthetically by solid phase peptide synthesis, including, for example the methods of synthesis disclosed in Merrifield (1963) or Knorr et al. (1989). Examples of peptide synthesis also include the synthesis methods used by peptide synthesisers of Perkin Elmer/Applied Biosystems, CA, US.

In another aspect, the invention provides a polynucleotide sequence encoding a hybrid molecule of the invention.

In another aspect, the invention provides a hybrid molecule which comprises a synthetic polymer which is linked in a tropoelastin derivative comprising the amino acid sequence of peptide 26A, or an amino acid sequence variant of the derivative comprising the amino acid sequence of peptide 26A.

The invention further provides a method of imparting or enhancing GAG binding activity to a biological polymer comprising the step of linking a tropoelastin derivative comprising the amino acid sequence of peptide 26A, or an amino acid sequence variant of peptide 26A with the biological polymer. Preferably the biological polymer is a protein.

The invention further provides a method of deleting or reducing GAG binding activity from a biological polymer comprising the step of deleting a tropoelastin derivative comprising the amino acid sequence of peptide 26A, or an amino acid sequence variant of peptide 26A from the biological polymer. Preferably the biological polymer is a protein.

The present invention also provides a tropoelastin derivative comprising the amino acid sequence of SHELgamma. SHELgamma has the amino acid sequence:

(SEQ ID NO: 9)
SAMGALVGLGVPGLGVGAGVPGFGAGADEGVRRSLSPELREGDPSSSQHL

PSTPSSPRVPGALAAAKAAKYGAAVPGVLGGLGALGGVGIPGGVVGAGPA

AAAAAAKAAAKAAQFGLVGAAGLGGLGVGGLGVPGVGGLGGIPPAAAAKA

AKYGAAGLGGVLGGAGQFPLGGVAARPGFGLSPIFPGGACLGKACGRKR

K.

The invention also provides an amino acid sequence variant of the derivative comprising the amino acid sequence of SHELgamma.

The invention also provides a polynucleotide encoding a tropoelastin derivative, the derivative comprising the amino acid sequence of SHELgamma. The nucleotide sequence of the polynucleotide SHELgamma (SEQ ID NO: 8) is shown in FIG. 8. In this nucleotide sequence, the first 9 codons from nucleotide position 948 to 974 are derived from the glutathione S-transferase (GST) fusion nucleotide sequence. Preferably the polynucleotide comprises the nucleotide sequence shown in FIG. 8. More preferably the polynucleotide comprises the nucleotide sequence shown in FIG. 8 from nucleotide sequence position 975 to 1547.

The invention also provides a polynucleotide encoding an amino acid sequence variant of the derivative comprising the amino acid sequence of SHELgamma.

The present invention also provides a polynucleotide encoding a tropoelastin derivative, the derivative comprising the amino acid sequence of SHELgamma excluding exon 26A. The nucleotide sequence of the polynucleotide SHELgamma excluding exon 26A (SEQ ID NO: 6) is shown in FIG. 7. In this nucleotide sequence, the first 5 codons from nucleotide position 948 to 962 are derived from the GST nucleotide sequence. SHELgamma excluding exon 26A has the following amino acid sequence:

(SEQ ID NO: 7)
VPGALAAAKAAKYGAAVPGVLGGLGALGGVGIPGGVVGAGPAAAAAAKA

AAKAAQFGLVGAAGLGGLGVGGLGVPGVGGLGGIPPAAAAKAAKYGAAGL

GGVLGGAGQFPLGGVAARPGFGLSPIFPGGACLGKACGRKRK.

Preferably the polynucleotide comprises the nucleotide sequence shown in SEQ ID NO:6. More preferably the polynucleotide comprises the nucleotide sequence shown in SEQ ID NO:6 from nucleotide sequence position 15 to 441.

The invention also provides a polynucleotide encoding an amino acid sequence variant of the derivative comprising the amino acid sequence of SHELgamma excluding exon 26A.

The invention also provides a tropoelastin derivative comprising the amino acid sequence of SHELgamma excluding exon 26A.

The invention also provides an amino acid sequence variant of the derivative comprising SHELgamma excluding exon 26A.

The derivatives of the invention based on SHELgamma can also be produced by in vitro biochemical cleavage of tropoelastin products such as SHEL, so as to release a carboxy-terminal fragment. The carboxy-terminal fragment may be purified by reverse phase HPLC.

The present invention also provides a tropoelastin derivative comprising the amino acid sequence of SHEL31-36. SHEL31-36 has the following amino acid sequence:

(SEQ ID NO: 10)
GIPPAAAAKAAKYGAAGLGGVLGGAGQFPLGGVAARPGFGLSPIFPGGAC

LGKACGRKRK.

SHEL31-36 retains a crosslinking domain. As a consequence of its elastin-like properties, it is envisaged that this and related tropoelastin derivatives can be used to interfere with tropoelastin deposition and formation of unaltered elastic fibre.

The invention also provides an amino acid sequence variant of the derivative comprising the amino acid sequence of SHEL31-36.

The invention also provides a polynucleotide encoding a tropoelastin derivative, the derivative comprising the amino acid sequence of SHEL31-36. Preferably the polynucleotide comprises the nucleotide sequence shown in FIG. 1 (SEQ ID NO:1) from nucleotide position 2022 to 2210.

The invention also provides a polynucleotide encoding an amino acid variant of the derivative comprising the amino acid sequence of SHEL31-36.

The present invention also provides a tropoelastin derivative, comprising the amino acid sequence of SHEL32-36. SHEL32-36 has the following amino acid sequence:

(SEQ ID NO: 11)
GAAGLGGVLGGAGQFPLGGVAARPGFGLSPIFPGGACLGKACGRKRK.

The invention also provides an amino acid sequence variant of the derivative comprising the amino acid sequence of SHEL32-36.

The invention also provides a polynucleotide encoding a tropoelastin derivative, the derivative comprising the amino acid sequence of SHEL32-36. Preferably the polynucleotide comprises the nucleotide sequence shown in FIG. 1 (SEQ ID NO: 1) from nucleotide position 2061 to 2210.

The present invention also provides a polynucleotide encoding an amino acid sequence variant of the derivative comprising the amino acid sequence of SHEL32-36.

As a consequence of its elastin-like properties, it is envisaged that SHEL32-36 and related tropoelastin derivatives can be used to interfere with tropoelastin deposition and formation of an unaltered elastic fibre.

The present invention also provides a tropoelastin derivative, comprising the amino acid sequence of SHEL26-36. SHEL26-36 has the following amino acid sequence:

(SEQ ID NO: 14)
AAAGLGAGIPGLGVGVGVPGLGVGAGVPGLGVGAGVPGFGAGADEGVRRS

LSPELREGDPSSSQHLPSTPSSPRVPGALAAAKAAKYGAAVPGVLGGLGA

-continued

LGGVGIPGGVVGAGPAAAAAAAKAAAKAAQFGLVGAAGLGGLGVGGLGVP

GVGGLGGIPPAAAAKAAKYGAAGLGGVLGGAGQFPLGGVAARPGFGLSPI

FPGGACLGKACGRKRK

The invention also provides an amino acid sequence variant of the derivative comprising the amino acid sequence of SHEL26-36.

The invention also provides a polynucleotide encoding a tropoelastin derivative, the derivative comprising the amino acid sequence of SHEL26-36. Preferably the polynucleotide comprises the nucleotide sequence shown in FIG. 1 from nucleotide position 1554-2210.

The present invention also provides a tropoelastin derivative, comprising the amino acid sequence of SHEL26-36 excluding exon 26A. SHEL26-36 excluding exon 26A has the following amino acid sequence:

(SEQ ID NO: 15)
AAAGLGAGIPGLGVGVGVPGLGVGAGVPGLGVGAGVPGFGAVPGALAAAK

AAKYGAAVPGVLGGLGALGGVGIPGGVVGAGPAAAAAAAKAAAKAAQFGL

VGAAGLGGLGVGGLGVPGVGGLGGIPPAAAAKAAKYGAAGLGGVLGGAGQ

FPLGGVAARPGFGLSPIFPGGACLGKACGRKRK

The invention also provides an amino acid sequence variant of the derivative comprising the amino acid sequence of SHEL26-36 excluding exon 26A.

The invention also provides a polynucleotide encoding a tropoelastin derivative, the derivative comprising the amino acid sequence of SHEL26-36 excluding exon 26A. Preferably the polynucleotide comprises the nucleotide sequence shown in FIG. 1 from nucleotide position 1554 to 1676 contiguous with 1776 to 2210.

The present invention also provides a polynucleotide encoding an amino acid sequence variant of the derivative comprising the amino acid sequence of SHEL26-36.

In another aspect the present invention provides a formulation comprising a tropoelastin derivative, a variant of the derivative or a hybrid molecule of the invention, together with a carrier or diluent.

Formulations of the derivatives, variants or hybrid molecules of the invention can be prepared in accordance with standard techniques appropriate to the field in which they are to be used.

The polynucleotides and synthetic polynucleotides of the invention can be provided in association with other polynucleotide sequences including 5' and 3' untranslated sequences, and 5' upstream and 3' downstream transcriptional regulatory sequences. The polynucleotides and synthetic polynucleotides may be provided as a recombinant DNA molecule including plasmid DNA.

The polynucleotides and synthetic polynucleotides of the invention can be prepared using the techniques of chemical synthesis or recombinant DNA technology, or by a combination of both techniques.

In a further aspect the invention provides a vector comprising a polynucleotide or synthetic polynucleotide encoding a tropoelastin derivative, a variant of the derivative or a hybrid molecule of the invention.

Vectors useful in this invention include plasmids, phages and phagemids. The polynucleotides and synthetic polynucleotides of the present invention can also be used in integrative expression systems or lytic or comparable expression systems.

Suitable vectors will generally contain origins of replication and control sequences which are derived from species compatible with the intended expression host. Typically these vectors include a promoter located upstream from the polynucleotide, together with a ribosome binding site if intended for prokaryotic expression, and a phenotypic selection gene such as one conferring antibiotic resistance or supplying an auxotrophic requirement. For production vectors, vectors which provide for enhanced stability through partitioning may be chosen. Where integrative vectors are used it is not necessary for the vector to have an origin of replication. Lytic and other comparable expression systems do not need to have those functions required for maintenance of vectors in hosts.

For *E. coli* typical vectors include pBR322, pBluescript II SK+, pGEX-2T, pTrc99A, pET series vectors, particularly pET3d, (Studier et al., 1990) and derivatives of these vectors. Derivatives include those plasmids with a modified protease recognition sequence to facilitate purification of a protein domain.

In another aspect the invention provides a cell capable of expressing a polynucleotide or a synthetic polynucleotide which encodes a derivative or variant of the invention, or a polynucleotide which encodes a hybrid molecule of the invention.

A preferred expression system is an *E. coli* expression system. However, the invention includes within its scope the use of other hosts capable of expressing protein from the polynucleotides designed for use in *E. coli*. The invention also includes the use of polynucleotides and synthetic polynucleotides suitable for use in other expression systems such as other microbial expression systems. These other expression systems include yeast, and bacterial expression systems, insect cell expression systems, and expression systems involving other eukaryotic cell lines or whole organisms.

Examples of *E. coli* hosts include *E. coli* B strain derivatives (Studier et al, 1990), and K-strain derivatives such as NM522 (Gough and Murray, 1983) and XL1-Blue (Bullock et al, 1987).

In a further aspect the present invention provides an expression product. In the specification and claims, "expression product" means a derivative or variant of the invention expressed by a cell containing a polynucleotide or a synthetic polynucleotide encoding a derivative or variant of the invention.

The expression products of the invention may be fused expression products which include all or part of a protein encoded by the vector in peptide linkage with the derivative or variant. They may also include, for example, an N-terminal methionine or other additional residues which do not permanently impair the elastin-like, or macro-molecular binding properties of the product.

Typically the fusion is to the N-terminus of the expression product. An example of a suitable protein is to the C-terminus of glutathione S-transferase. The fused protein sequence may be chosen in order to cause the expression product to be secreted or expressed as a cell surface protein to simplify purification or expressed as a cytoplasmic protein.

The expressed fusion products may subsequently be treated to remove the fused protein sequences to provide free tropoelastin derivative or variant. Treatment is typically through protease treatment or, in the case of secretion, removal is effected by endogenous host secretion machinery. An example of this is secretion by yeasts.

Non-fused systems include the introduction of or use of a pre-existing methionine codon. An example of this is the use of pET3a or pET3d in *E. coli*.

In another aspect the invention provides a polynucleotide encoding an expression product of the invention.

In another aspect the present invention provides a formulation comprising an expression product of the invention together with a carrier or diluent. The formulation of the expression product can be prepared in accordance with standard techniques appropriate to the field in which they are to be used.

According to a further aspect of the present invention there is provided a method for producing a tropoelastin derivative or a variant of the derivative comprising providing a vector containing a polynucleotide or a synthetic polynucleotide encoding the derivative or variant; introducing the vector into a suitable host cell; maintaining the cell in conditions suitable for expression of the polynucleotide or synthetic polynucleotide and isolating the derivative or variant of the invention. The method can be applied to the production of the expression products and hybrid molecules (in which the hybrid molecules comprise the peptide 26A or a variant thereof and a further amino acid sequence) of the invention, by providing a vector containing a polynucleotide encoding an expression product or a hybrid molecule; introducing the vector into a suitable host cell; maintaining the cell in conditions suitable for expression of the polynucleotide and isolating the expression product or hybrid molecule.

In one embodiment, the polynucleotide or synthetic polynucleotide encoding the derivative, variant, expression product or hybrid molecule of the invention is expressed in a host cell which is maintained in culture in vitro.

Alternatively, the polynucleotide or synthetic polynucleotide encoding the derivative, variant, expression product or hybrid molecule of the invention is expressed in a host cell which is maintained in vivo. Thus, in another embodiment, the polynucleotide or synthetic polynucleotide encoding the derivative, variant, expression product or hybrid molecule of the invention is expressed in a transgenic animal. Methods for the generation of transgenic animals are known in the art. Exemplary methods are described in Slack et al. 1991 and Janne et al. 1992.

The tropoelastin derivatives, variants of the derivatives, and hybrid molecules (in which the hybrid molecules comprise the peptide 26A or a variant thereof and a further amino acid sequence) of the invention may be produced by solid phase peptide synthesis, including, for example, the methods of synthesis disclosed in Merrifield (1963) or Knorr et al (1989). Examples of peptide synthesis also include the synthesis methods used by peptide synthesisers of Perkin Elmer/ Applied Biosystems, Calif., US. As an alternative to cell synthesis from a polynucleotide or synthetic polynucleotide, the expression products of the invention may be produced by solid phase peptide synthesis.

In a further aspect the present invention provides an implant formed from at least one tropoelastin derivative and/ or variant of the derivative of the invention. The implant may alternatively contain at least one expression product and/or at least one hybrid molecule of the invention.

The implants are formed into the required shape by cross-linking the tropoelastin derivative, variant of the derivative, expression product, or hybrid molecule of the invention, in a mould which conforms to the desired shape of the implant. Where the implant is required to be used in sheet form the tropoelastin derivative, variant of the derivative, expression product, or hybrid molecule of the invention can be cross-linked on a flat surface. Relevant methodologies are described in, for example, U.S. Pat. No. 4,474,851 and U.S. Pat. No. 5,250,516. The elastomeric materials may be exclusively prepared from one or more tropoelastin derivatives, variants of the derivative, expression products, or hybrid molecules of the invention or may be composites prepared from one or more of these constituents together with other materials.

The tropoelastin derivatives or variants of the derivatives can be cross-linked to form elastin or elastin-like material or can be cross-linked in conjunction with other biological or synthetic molecules to form a composite material.

Thus in another aspect the invention provides a cross-linked complex which comprises at least one tropoelastin derivative of the invention and/or at least one variant of a derivative of the invention. The cross-linked complexes may additionally contain at least one expression product and/or at least one hybrid molecule of the invention, which may be cross-linked to the at least one tropoelastin derivative and/or variant of the derivative of the invention.

The cross-linking of the tropoelastin derivatives, variants of the derivatives, hybrid molecules and expression products of the invention can be achieved by chemical oxidation of lysine side chains using processes such as ruthenium tetroxide mediated oxidation and quinone mediated oxidation, or by using homobifunctional chemical cross-linking agents such as dithiobis (succinimidylpropionate), dimethyl adipimidate or dimethyl pimelimidate. Glutaraldehyde cross-linking is an important addition to this repetoire. Another alternative is the cross-linking of lysine and glutamic side chains.

The tropoelastin derivatives, variants of the derivatives, hybrid molecules and expression products of the invention may also be enzymatically cross-linked by methods including lysyl oxidase mediated oxidation or may be cross-linked using gamma irradiation.

BRIEF DESCRIPTION OF THE DRAWINGS

FIGS. 1A-1J: Nucleotide (SEQ ID NO: 1) and predicted amino acid (SEQ ID NO:2) sequences of synthetic human tropoelastin SHEL. The upper (numbered) nucleotide sequence represents the coding strand.

FIGS. 2A-2B: Alignment of SHEL (SEQ ID NO:2)(upper line) and SHELδ26A (SEQ ID NO: 3) amino acid sequences.

FIGS. 3A-3F: Nucleotide (SEQ ID NO: 4) and predicted amino acid (SEQ ID NO: 5) sequences of SHELδmodified.

FIGS. 4A-4F: Alignment of SHELδmodified (SEQ ID NO: 4) (upper line) and SHEL (SEQ ID NO:1) nucleotide sequences.

FIGS. 5A-5D: Alignment of SHELδmodified (SEQ ID NO: 5)(lower line) and SHEL (SEQ ID NO: 1) amino acid sequences.

FIG. 7: Nucleotide (SEQ ID NO: 6) and predicted amino acid (SEQ ID NO: 7) sequences of SHELgamma excluding exon 26A.

FIGS. 8A-8B: Nucleotide (SEQ ID NO: 8) and predicted amino acid (SEQ ID NO: 9) sequences of SHELgamma.

FIG. 9 is a key showing the drawing sheets of FIGS. 1A-5D.

BEST METHOD OF PERFORMING THE INVENTION

Figure 6A:
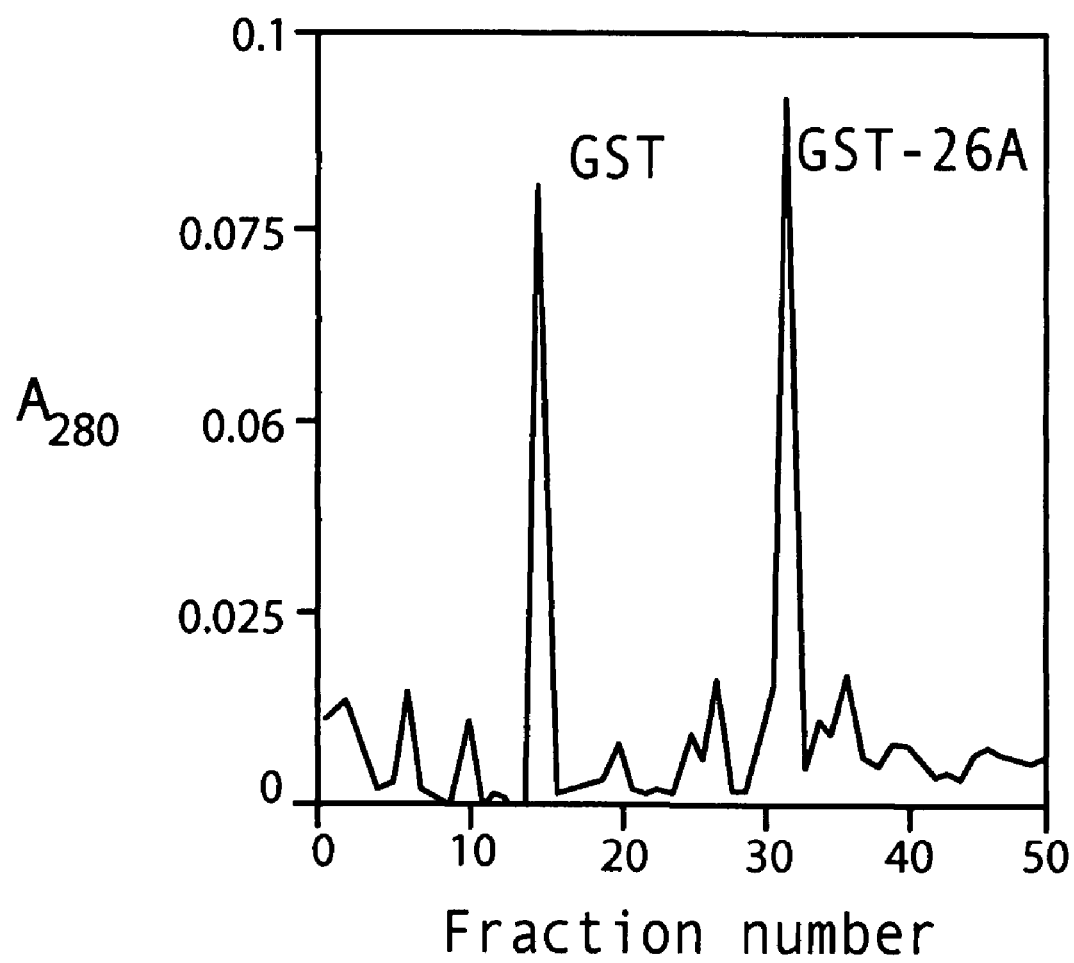
FIG. 6A: HPLC elution profile of GST-exon 26A fusion protein tropoelastin derivative loaded in from heparin sepharose. 6B: Binding of peptide 26A (SEQ ID NO: 12 and SEQ ID NO: 13) to glycosaminoglycans.

The recombinant and synthetic procedures used for the synthesis of the derivatives, variants, expression products and hybrid molecules of the invention are described in standard texts such as Sambrook et al (1989).

Tropoelastin nucleotide sequences may be modified so as to provide derivatives, variants, expression products or hybrid molecules, by conventional site-directed or random mutagenesis. The sequences may also be modified by oligonucleotide-directed mutagenesis, which comprises the following steps:

1. synthesis of an oligonucleotide with a sequence that contains the desired nucleotide substitution (mutation);
2. hybridising the oligonucleotide to a template comprising a structural sequence encoding tropoelastin; and
3. using a DNA polymerase to extend the oligonucleotide as a primer.

Another approach which is particularly suited to situations where a synthetic polynucleotide encoding the tropoelastin derivative is prepared from oligonucleotide blocks bounded by restriction sites, is cassette mutagenesis where entire restriction fragments are replaced.

Purification of the derivatives, variants, expression products or hybrid molecules of the invention is performed using standard techniques including HPLC. The actual sequence of steps in the purification of a particular derivative, variant, expression product or hybrid molecule is limited by the environment from which the molecule is to be purified. By way of example, reference is made to the purification scheme disclosed in WO94/14958.

Formulations in accordance with the invention are formulated in accordance with standard techniques.

The amount of derivative, variant, expression product or hybrid molecule that may be combined with a carrier or diluent to produce a single dosage will vary depending on the situation in which the formulation is to be used and the particular mode of administration.

It will be understood also that specific doses for any particular host may be influenced by factors such as the age, sex, weight and general health of the host as well as the particular characteristics of the derivative, variant, expression product or hybrid molecule of the invention being used, and how it is administered.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a non-toxic parenterally acceptable diluent or solvent. Among the acceptable vehicles or solvents that may be employed are water, Ringer's solution, alcohols and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid and organic solvents find use in the preparation of injectables.

Routes of administration, dosages to be administered as well as frequency of administration are all factors which can be optimised using ordinary skill in the art.

In addition, the derivatives, variants, expression products and hybrid molecules of the invention may be prepared as topical preparations for instance as anti-wrinkle and hand lotions using standard techniques for the preparation of such formulations. They may be prepared in aerosol form for, for instance, administration to a patient's lungs, or in the form of surgical implants, foods or industrial products by standard techniques.

SHEL

The preparation of SHEL is described in WO94/14958. It is directly expressed as a full length human protein with a calculated molecular weight of 64 kDa. The full nucleotide sequence and corresponding amino acid sequence of SHEL is shown in FIG. 1. The preparation of pSHELF is described in WO94/14958.

pSHELF differs from the natural coding sequence(s) in a number of ways. As described in WO94/14958, the untranslated regions present in the tropoelastin cDNA sequence were disregarded in designing the synthetic gene, and the nucleotides encoding the signal peptide were removed. Restriction endonuclease recognition sites were incorporated at regular intervals into the gene by typically altering only the third base of the relevant codons, thereby maintaining the primary sequence of the gene product. The facility for silent alteration of the coding sequence was also exploited to change the codon bias of the tropoelastin gene to that commonly found in highly expressed *E. coli* genes. [Genetics Computer Group (GCG) package version 7-UNIX using Codon Frequency and Gen Run Data: ecohigh-cod]. Two additional stop codons were added to the 3'-end, and an ATG start codon comprising a novel NcoI site was appended to the 5'-end. Bam HI cloning sites were engineered at both ends of the synthetic sequence. Since the gene contains no internal methionine residues, treatment of the newly-synthesized gene product (expressed directly or as a fusion with another gene) with cyanogen bromide would liberate a protein with the same or similar sequence as one form of natural tropoelastin comprising 731 amino acids. Other forms of processing are envisaged, which may generate tropoelastin species of the same or different lengths.

Two stop codons were added in order to allow the possible use of the construct in suppressor hosts, and also to avoid any potential depletion of termination (release) factors for translation As described in the following examples, the derivatives, pSHELFδ26A, pSHELFδ modified, pSHELgamma, pSHEL31-36, pSHEL32-36 and pSHELgammaδ26A were derived from the pSHELF nucleotide sequence. These particular derivatives, and indeed the derivatives, variants, expression products and hybrid molecules of the invention can equally be derived from a native human or non-human tropoelastin nucleotide sequence.

Example 1

Construction of pSHELFδ26A and pSHELFδModified

Mutagenesis was used with PSHELF to remove DNA corresponding to exon 26A. The sequence of the mutagenic primer was:

(SEQ ID NO: 16)
5'CGG GTT TCG GTG CTG TTC CGG GCG CGC TGG 3'

This flanked either side of exon 26A by 15 bp resulting in its precise deletion. A second selection primer, which mutates a unique restriction site to another restriction site is normally used in the protocol but was not in this case since deletion of exon 26A also resulted in the deletion of a unique restriction site, PmlI. The enzyme PmlI was used to treat the mutation reaction to linearise any unmutated parental plasmid and consequently to enrich for mutant plasmid. The reaction mixture was used to transform competent BMH17-18 mutS *E. coli*, defective in mismatch repair, by electroporation and the entire transformed culture was grown overnight in LB+ampicillin. Mixed plasmid DNA, containing both mutated and parental plasmids, was isolated from the culture and the plasmid DNA was digested with PmlI to linearise the parental plasmid. The plasmid DNA, now enriched for mutated plasmid, was used to transform *E. coli* HMS174 by electroporation and transformants selected on LB plates containing 75 µgml$^{-1}$ ampicillin.

Colonies were grown overnight and plasmid mini-preparations performed. Constructs were screened using PmlI and those which were insensitive to digestion were further screened by KpnI/PstI double digestion. Candidate clones were sequenced to verify the sequence, named pSHELFδ-modified.

Sequencing confirmed the region immediately surrounding the deletion was correct. PstI and BssHII restriction sites surrounding the correct region of pSHELδmodified were used to remove the desired segment and re-insert it into the corresponding site of pSHELF. 6.5 µg PSHELF and 7.5 µg pSHELFδmodified were digested with BssHII, precipitated and digested with PstI. The appropriate three fragments were gel-purified and ligated. DNA was transformed into *E. coli* XL1-Blue and transformants selected on plates containing 75 µgml.sup.-1 ampicillin.

Plasmids were isolated by mini-preparations and screened using BglI digestion. A candidate clone was further analysed by restriction enzyme digestion and sequenced, and named pSHELFδ26A.

Example 2

Synthesis of Exon 26A

The region of SHEL corresponding to exon 26A was amplified by PCR, with primers modified to introduce an in-frame BamHII site upstream and a stop codon downstream at the 3' end. Two forms were generated: one terminating in valine (26AV) and the other terminating in phenyalanine (26AF). These forms are as follows:

```
                                           (SEQ ID NO: 12)
     GADEGVRRSLSPELREGDPSSSQHLPSTPSSPRV
``` with properties:
  Molecular weight=3588.80
  Residues=34
  Average Residue Weight=105.553
  Charge=−1
  Isoelectric point=5.71
and

```
                                           (SEQ ID NO: 13)
     GADEGVRRSLSPELREGDPSSSQHLPSTPSSPRF
```

A 26A coding region was expressed as a glutathione S-transferase (GST) fusion protein.

Example 3

Glycosaminoglycan Binding Activity of Exon 26A

Ultrafiltration assay methodology was developed to examine and quantify interactions occurring in vitro between the 26A region and purified extracellular matrix glcosaminoglycans. GST26A fusion protein and tropoelastin were compared with GST and tropoelastin lacking exon 26A at physiologically relevant conditions of pH and ionic strength.

Figure 6B:
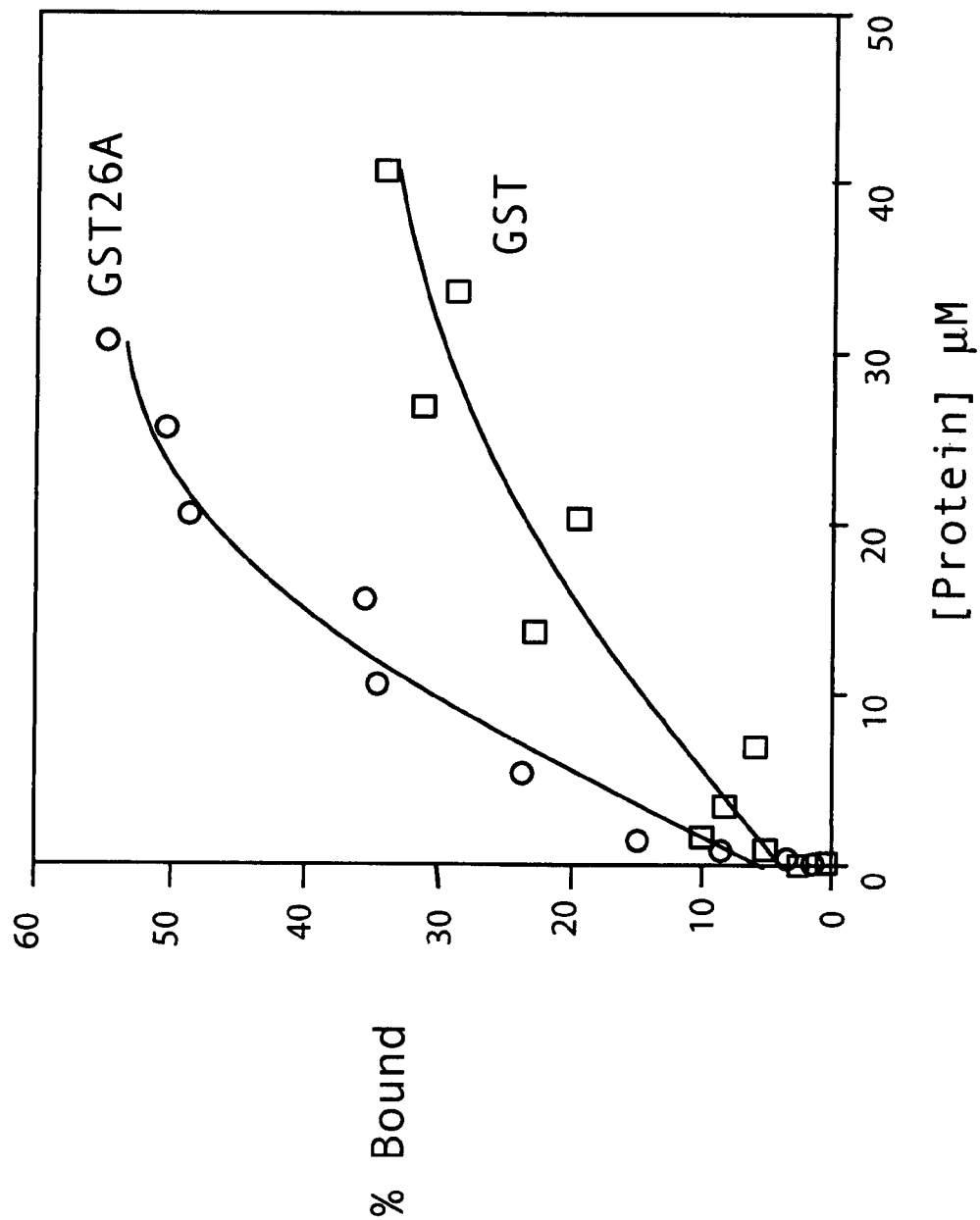

Experimental evidence supports the notion that peptide 26A (26AF and 26AV) binds GAGs. Immobilised heparin column binding shows that GST26A binds more tightly than does GST, and requires a higher sodium chloride concentration for elution (FIG. 6B). Furthermore, GST26A fusion protein binds radioactive heparin with greater efficiencies than GST, and these can be compared with GAGs including chondroitin sulphates and keratin sulphates. An implication of this is that GAGs binding to tropoelastin can be adjusted based upon the content of 26A. Cross-linked tropoelastin would be expected to show differential binding to GAGs based on the relative amounts of SHEL vs. SHEL526A.

In summary, these studies reveal that the 26A region is a functional glycosaminoglycan binding domain, which functions in intact tropoelastin. It is also active when isolated as a fusion entity yet displays no detectable structure in the absence of bound GAG. Furthermore, panel competition studies indicate a preference for those GAGs found in close association with the elastic fibre in the extracellular matrix.

Example 4

Construction of pSHELgamma, pSHEL31-36, pSHEL32-36 and pSHELgammaδ26A pSHELgamma is derived from the pSHELgamma construct disclosed in WO94/14958. pSHEL31-36, pSHEL32-36 and pSHELgammaδ26A were derived from pSHELgamma. pSHELgamma was modified by introducing an oligonucleotide linker at the KpnI site. This encoded a factor Xa cleavage site which could be utilised in subsequent constructs. PCR and site directed mutagenesis was then used to generate further, shorter forms which provided fusions with GST. Constructs were DNA sequenced for verification. Induced protein was isolated as GST-fusion proteins, which were subsequently bound to glutathione agarose. Protease cleavage was optional where fusion proteins were desired; otherwise the cleaved proteins and peptides were further purified by reverse phase HPLC.

INDUSTRIAL APPLICATION

The derivatives and expression products of the invention are of use in inter alia the medical, pharmaceutical, veterinary and cosmetic fields.

---

The invention claimed is:

1. An isolated polynucleotide encoding a tropoelastin polypeptide wherein the polynucleotide has one or more of the following sequences:
   (a) the nucleotide sequence from position 9 to position 1676 of SEQ ID NO:1 contiguous with position 1776 to 2201 of SEQ ID NO:1;
   (b) the nucleotide sequence from position 1554 to 1676 of SEQ ID NO: 1 contiguous with 1776 to 2201 of SEQ ID NO: 1; and
   (c) the nucleotide sequence from position 1663 to 1676 contiguous with 1776 to 1791 of SEQ ID NO: 1.

2. An expression vector comprising the polynucleotide of claim 1.

3. An isolated cell transformed with the vector of claim 2.

4. A method for producing a tropoelastin polypeptide, comprising:
   introducing the vector of claim 2 into a suitable host cell, and maintaining the cell under conditions suitable for expression of the tropoelastin polypeptide.

5. The polynucleotide of claim 1 comprising:
   the nucleotide sequence from position 9 to position 1676 of SEQ ID NO: 1 contiguous with position 1776 to 2201 of SEQ ID NO: 1.

6. The polynucleotide of claim 1 having the nucleotide sequence from position 1554 to 1676 of SEQ ID NO: 1 contiguous with position 1776 to 2201 of SEQ ID NO: 1.

7. The polynucleotide of claim 1 having the nucleotide sequence from position 1663 to 1676 contiguous with position 1776 to 1791 of SEQ ID NO: 1.

* * * * *

SEQUENCE LISTING

<160> NUMBER OF SEQ ID NOS: 16

<210> SEQ ID NO 1
<211> LENGTH: 2210
<212> TYPE: DNA
<213> ORGANISM: ARTIFICIAL
<220> FEATURE:

-continued

<223> OTHER INFORMATION: Synthetic polynucleotide sequence encoding human tropolelastin

<400> SEQUENCE: 1

| | | | | | |
|---|---|---|---|---|---|
| gatccatggg | tggcgttccg | ggtgctatcc | cgggtggcgt | tccgggtggt | gtattctacc | 60 |
| caggcgcggg | tctgggtgca | ctgggcggtg | gtgcgctggg | cccgggtggt | aaaccgctga | 120 |
| aaccggttcc | aggcggtctg | gcaggtgctg | gtctgggtgc | aggtctgggc | gcgttcccgg | 180 |
| cggttacctt | cccgggtgct | ctggttccgg | gtggcgttgc | agacgcagct | gctgcgtaca | 240 |
| aagcggcaaa | ggcaggtgcg | ggtctgggcg | gggtaccagg | tgttggcggt | ctgggtgtat | 300 |
| ctgctggcgc | agttgttccg | cagccgggtg | caggtgtaaa | accgggcaaa | gttccaggtg | 360 |
| ttggtctgcc | gggcgtatac | ccgggtggtg | ttctgccggg | cgcgcgtttc | ccaggtgttg | 420 |
| gtgtactgcc | gggcgttccg | accggtgcag | gtgttaaacc | gaaggcacca | ggtgtaggcg | 480 |
| gcgcgttcgc | gggtatcccg | ggtgttggcc | cgttcggtgg | tccgcagcca | ggcgttccgc | 540 |
| tgggttaccc | gatcaaagcg | ccgaagcttc | caggtggcta | cggtctgccg | tacaccaccg | 600 |
| gtaaactgcc | gtacggctac | ggtccgggtg | gcgtagcagg | tgctgcgggt | aaagcaggct | 660 |
| acccaaccgg | tactggtgtt | ggtccgcagg | ctgctgcggc | agctgcggcg | aaggcagcag | 720 |
| caaaattcgg | cgcgggtgca | gcgggtgttc | tgccgggcgt | aggtggtgct | ggcgttccgg | 780 |
| gtgttccagg | tgcgatcccg | ggcatcggtg | gtatcgcagg | cgtaggtact | ccggcggccg | 840 |
| ctgcggctgc | ggcagctgcg | gcgaaagcag | ctaaatacgg | tgcggcagca | ggcctggttc | 900 |
| cgggtggtcc | aggcttcggt | ccgggtgttg | taggcgttcc | gggtgctggt | gttccgggcg | 960 |
| taggtgttcc | aggtgcgggc | atcccggttg | taccgggtgc | aggtatcccg | ggcgctgcgg | 1020 |
| ttccaggtgt | tgtatccccg | gaagcggcag | ctaaggctgc | tgcgaaagct | gcgaaatacg | 1080 |
| gagctcgtcc | gggcgttggt | gttggtggca | tcccgaccta | cggtgtaggt | gcaggcggtt | 1140 |
| tcccaggttt | cggcgttggt | gttggtggca | tcccgggtgt | agctggtgtt | ccgtctgttg | 1200 |
| gtggcgtacc | gggtgttggt | ggcgttccag | gtgtaggtat | ctccccggaa | gcgcaggcag | 1260 |
| ctgcggcagc | taaagcagcg | aagtacgcg | ttggtactcc | ggcggcagca | gctgctaaag | 1320 |
| cagcggctaa | agcagcgcag | ttcggactag | ttccgggcgt | aggtgttgcg | ccaggtgttg | 1380 |
| gcgtagcacc | gggtgttggt | gttgctccgg | gcgtaggtct | ggcaccgggt | gttggcgttg | 1440 |
| caccaggtgt | aggtgttgcg | ccgggcgttg | gtgtagcacc | gggtatcggt | ccgggtggcg | 1500 |
| ttgcggctgc | tgcgaaatct | gctgcgaagg | ttgctgcgaa | agcgcagctg | cgtgcagcag | 1560 |
| ctggtctggg | tgcgggcatc | ccaggtctgg | gtgtaggtgt | tggtgttccg | ggcctgggtg | 1620 |
| taggtgcagg | ggtaccgggc | ctgggtgttg | gtgcaggcgt | tccgggtttc | ggtgctggcg | 1680 |
| cggacgaagg | tgtacgtcgt | tccctgtctc | agaactgcg | tgaaggtgac | ccgtcctctt | 1740 |
| cccagcacct | gccgtctacc | ccgtcctctc | cacgtgttcc | gggcgcgctg | gctgctgcga | 1800 |
| aagcggcgaa | atacggtgca | gcggttccgg | gtgtactggg | cggtctgggt | gctctgggcg | 1860 |
| gtgttggtat | cccgggcggt | gttgtaggtg | caggcccagc | tgcagctgct | gctgcggcaa | 1920 |
| aggcagcggc | gaaagcagct | cagttcggtc | tggttggtgc | agcaggtctg | ggcggtctgg | 1980 |
| gtgttggcgg | tctgggtgta | ccggcgcgttg | gtggtctggg | tggcatcccg | ccggcggcgg | 2040 |
| cagctaaagc | ggctaaatac | ggtgcagcag | gtctgggtgg | cgttctgggt | ggtgctggtc | 2100 |
| agttccacct | gggcggtgta | gcggcacgtc | cgggtttcgg | tctgtccccg | atcttcccag | 2160 |
| gcggtgcatg | cctgggtaaa | gcttgcggcc | gtaaacgtaa | ataatgatag | | 2210 |

```
<210> SEQ ID NO 2
<211> LENGTH: 733
<212> TYPE: PRT
<213> ORGANISM: HUMAN

<400> SEQUENCE: 2

Ser Met Gly Gly Val Pro Gly Ala Ile Pro Gly Gly Val Pro Gly Gly
1               5                   10                  15

Val Phe Tyr Pro Gly Ala Gly Leu Gly Ala Leu Gly Gly Gly Ala Leu
            20                  25                  30

Gly Pro Gly Gly Lys Pro Leu Lys Pro Val Pro Gly Gly Leu Ala Gly
        35                  40                  45

Ala Gly Leu Gly Ala Gly Leu Gly Ala Phe Pro Ala Val Thr Phe Pro
    50                  55                  60

Gly Ala Leu Val Pro Gly Gly Val Ala Asp Ala Ala Ala Ala Tyr Lys
65                  70                  75                  80

Ala Ala Lys Ala Gly Ala Gly Leu Gly Gly Val Pro Gly Val Gly Gly
                85                  90                  95

Leu Gly Val Ser Ala Gly Ala Val Val Pro Gln Pro Gly Ala Gly Val
            100                 105                 110

Lys Pro Gly Lys Val Pro Gly Val Gly Leu Pro Gly Val Tyr Pro Gly
        115                 120                 125

Gly Val Leu Pro Gly Ala Arg Phe Pro Gly Val Gly Val Leu Pro Gly
    130                 135                 140

Val Pro Thr Gly Ala Gly Val Lys Pro Lys Ala Pro Gly Val Gly Gly
145                 150                 155                 160

Ala Phe Ala Gly Ile Pro Gly Val Gly Pro Phe Gly Gly Pro Gln Pro
                165                 170                 175

Gly Val Pro Leu Gly Tyr Pro Ile Lys Ala Pro Lys Leu Pro Gly Gly
            180                 185                 190

Tyr Gly Leu Pro Tyr Thr Thr Gly Lys Leu Pro Tyr Gly Tyr Gly Pro
        195                 200                 205

Gly Gly Val Ala Gly Ala Ala Gly Lys Ala Gly Tyr Pro Thr Gly Thr
    210                 215                 220

Gly Val Gly Pro Gln Ala Ala Ala Ala Ala Ala Lys Ala Ala Ala
225                 230                 235                 240

Lys Phe Gly Ala Gly Ala Ala Gly Val Leu Pro Gly Val Gly Gly Ala
                245                 250                 255

Gly Val Pro Gly Val Pro Gly Ala Ile Pro Gly Ile Gly Gly Ile Ala
            260                 265                 270

Gly Val Gly Thr Pro Ala Ala Ala Ala Ala Ala Ala Ala Ala Ala Lys
        275                 280                 285

Ala Ala Lys Tyr Gly Ala Ala Ala Gly Leu Val Pro Gly Gly Pro Gly
    290                 295                 300

Phe Gly Pro Gly Val Val Gly Val Pro Gly Ala Gly Val Pro Gly Val
305                 310                 315                 320

Gly Val Pro Gly Ala Gly Ile Pro Val Val Pro Gly Ala Gly Ile Pro
                325                 330                 335

Gly Ala Ala Val Pro Gly Val Val Ser Pro Glu Ala Ala Ala Lys Ala
            340                 345                 350

Ala Ala Lys Ala Ala Lys Tyr Gly Ala Arg Pro Gly Val Gly Val Gly
        355                 360                 365

Gly Ile Pro Thr Tyr Gly Val Gly Ala Gly Gly Phe Pro Gly Phe Gly
    370                 375                 380
```

```
Val Gly Val Gly Gly Ile Pro Gly Val Ala Gly Val Pro Ser Val Gly
385                 390                 395                 400

Gly Val Pro Gly Val Gly Gly Val Pro Gly Val Gly Ile Ser Pro Glu
            405                 410                 415

Ala Gln Ala Ala Ala Ala Lys Ala Ala Lys Tyr Gly Val Gly Thr
        420                 425                 430

Pro Ala Ala Ala Ala Lys Ala Ala Lys Ala Ala Gln Phe Gly
        435                 440                 445

Leu Val Pro Gly Val Gly Val Ala Pro Gly Val Gly Val Ala Pro Gly
    450                 455                 460

Val Gly Val Ala Pro Gly Val Gly Leu Ala Pro Gly Val Gly Val Ala
465                 470                 475                 480

Pro Gly Val Gly Val Ala Pro Gly Val Gly Val Ala Pro Gly Ile Gly
            485                 490                 495

Pro Gly Gly Val Ala Ala Ala Lys Ser Ala Ala Lys Val Ala Ala
        500                 505                 510

Lys Ala Gln Leu Arg Ala Ala Gly Leu Gly Ala Gly Ile Pro Gly
    515                 520                 525

Leu Gly Val Gly Val Gly Val Pro Gly Leu Gly Val Gly Ala Gly Val
    530                 535                 540

Pro Gly Leu Gly Val Gly Ala Gly Val Pro Gly Phe Gly Ala Gly Ala
545                 550                 555                 560

Asp Glu Gly Val Arg Arg Ser Leu Ser Pro Glu Leu Arg Glu Gly Asp
                565                 570                 575

Pro Ser Ser Ser Gln His Leu Pro Ser Thr Pro Ser Ser Pro Arg Val
            580                 585                 590

Pro Gly Ala Leu Ala Ala Ala Lys Ala Ala Lys Tyr Gly Ala Ala Val
        595                 600                 605

Pro Gly Val Leu Gly Gly Leu Gly Ala Leu Gly Gly Val Gly Ile Pro
    610                 615                 620

Gly Gly Val Val Gly Ala Gly Pro Ala Ala Ala Ala Ala Ala Ala Lys
625                 630                 635                 640

Ala Ala Ala Lys Ala Ala Gln Phe Gly Leu Val Gly Ala Ala Gly Leu
            645                 650                 655

Gly Gly Leu Gly Val Gly Gly Leu Gly Val Pro Gly Val Gly Gly Leu
        660                 665                 670

Gly Gly Ile Pro Pro Ala Ala Ala Ala Lys Ala Ala Lys Tyr Gly Ala
        675                 680                 685

Ala Gly Leu Gly Gly Val Leu Gly Gly Ala Gly Gln Phe Pro Leu Gly
    690                 695                 700

Gly Val Ala Ala Arg Pro Gly Phe Gly Leu Ser Pro Ile Phe Pro Gly
705                 710                 715                 720

Gly Ala Cys Leu Gly Lys Ala Cys Gly Arg Lys Arg Lys
                725                 730

<210> SEQ ID NO 3
<211> LENGTH: 698
<212> TYPE: PRT
<213> ORGANISM: HUMAN

<400> SEQUENCE: 3

Gly Gly Val Pro Gly Ala Ile Pro Gly Gly Val Pro Gly Gly Val Phe
1               5                   10                  15

Tyr Pro Gly Ala Gly Leu Gly Ala Leu Gly Gly Gly Ala Leu Gly Pro
```

-continued

```
                    20                  25                  30
Gly Gly Lys Pro Leu Lys Pro Val Pro Gly Gly Leu Ala Gly Ala Gly
             35                  40                  45
Leu Gly Ala Gly Leu Gly Ala Phe Pro Ala Val Thr Phe Pro Gly Ala
         50                  55                  60
Leu Val Pro Gly Gly Val Ala Asp Ala Ala Ala Tyr Lys Ala Ala
 65                  70                  75                  80
Lys Ala Gly Ala Gly Leu Gly Gly Val Pro Gly Val Gly Leu Gly
                 85                  90                  95
Val Ser Ala Gly Ala Val Val Pro Gln Pro Ala Gly Val Lys Pro
             100                 105                 110
Gly Lys Val Pro Gly Val Gly Leu Pro Gly Val Tyr Pro Gly Gly Val
             115                 120                 125
Leu Pro Gly Ala Arg Phe Pro Gly Val Gly Val Leu Pro Gly Val Pro
             130                 135                 140
Thr Gly Ala Gly Val Lys Pro Lys Ala Pro Gly Val Gly Gly Ala Phe
145                 150                 155                 160
Ala Gly Ile Pro Gly Val Gly Pro Phe Gly Gly Pro Gln Pro Gly Val
                 165                 170                 175
Pro Leu Gly Tyr Pro Ile Lys Ala Pro Lys Leu Pro Gly Gly Tyr Gly
                 180                 185                 190
Leu Pro Tyr Thr Thr Gly Lys Leu Pro Tyr Gly Tyr Gly Pro Gly Gly
             195                 200                 205
Val Ala Gly Ala Ala Gly Lys Ala Gly Tyr Pro Thr Gly Thr Gly Val
             210                 215                 220
Gly Pro Gln Ala Ala Ala Ala Ala Ala Lys Ala Ala Ala Lys Phe
225                 230                 235                 240
Gly Ala Gly Ala Ala Gly Val Leu Pro Gly Val Gly Ala Gly Val
                 245                 250                 255
Pro Gly Val Pro Gly Ala Ile Pro Gly Ile Gly Ile Ala Gly Val
                 260                 265                 270
Gly Thr Pro Ala Ala Ala Ala Ala Ala Ala Ala Lys Ala Ala
             275                 280                 285
Lys Tyr Gly Ala Ala Ala Gly Leu Val Pro Gly Gly Pro Gly Phe Gly
             290                 295                 300
Pro Gly Val Val Gly Val Pro Gly Ala Gly Val Pro Gly Val Gly Val
305                 310                 315                 320
Pro Gly Ala Gly Ile Pro Val Val Pro Gly Ala Gly Ile Pro Gly Ala
                 325                 330                 335
Ala Val Pro Gly Val Val Ser Pro Glu Ala Ala Lys Ala Ala Ala
             340                 345                 350
Lys Ala Ala Lys Tyr Gly Ala Arg Pro Gly Val Gly Val Gly Gly Ile
             355                 360                 365
Pro Thr Tyr Gly Val Gly Ala Gly Gly Phe Pro Gly Phe Gly Val Gly
             370                 375                 380
Val Gly Gly Ile Pro Gly Val Ala Gly Val Pro Ser Val Gly Gly Val
385                 390                 395                 400
Pro Gly Val Gly Gly Val Pro Gly Val Gly Ile Ser Pro Glu Ala Gln
                 405                 410                 415
Ala Ala Ala Ala Ala Lys Ala Ala Lys Tyr Gly Val Gly Thr Pro Ala
             420                 425                 430
Ala Ala Ala Ala Lys Ala Ala Lys Ala Ala Gln Phe Gly Leu Val
             435                 440                 445
```

-continued

Pro Gly Val Gly Val Ala Pro Gly Val Gly Ala Pro Gly Val Gly
    450                 455                 460

Val Ala Pro Gly Val Gly Leu Ala Pro Gly Val Gly Val Ala Pro Gly
465                 470                 475                 480

Val Gly Val Ala Pro Gly Val Gly Val Ala Pro Gly Ile Gly Pro Gly
                485                 490                 495

Gly Val Ala Ala Ala Lys Ser Ala Ala Lys Val Ala Ala Lys Ala
            500                 505                 510

Gln Leu Arg Ala Ala Ala Gly Leu Gly Ala Gly Ile Pro Gly Leu Gly
    515                 520                 525

Val Gly Val Gly Val Pro Gly Leu Gly Val Gly Ala Gly Val Pro Gly
    530                 535                 540

Leu Gly Val Gly Ala Gly Val Pro Gly Phe Gly Ala Val Pro Gly Ala
545                 550                 555                 560

Leu Ala Ala Ala Lys Ala Ala Lys Tyr Gly Ala Ala Val Pro Gly Val
                565                 570                 575

Leu Gly Gly Leu Gly Ala Leu Gly Gly Val Gly Ile Pro Gly Gly Val
            580                 585                 590

Val Gly Ala Gly Pro Ala Ala Ala Ala Ala Ala Ala Lys Ala Ala Ala
    595                 600                 605

Lys Ala Ala Gln Phe Gly Leu Val Gly Ala Ala Gly Leu Gly Gly Leu
610                 615                 620

Gly Val Gly Gly Leu Gly Val Pro Gly Val Gly Gly Leu Gly Gly Ile
625                 630                 635                 640

Pro Pro Ala Ala Ala Ala Lys Ala Ala Lys Tyr Gly Ala Ala Gly Leu
                645                 650                 655

Gly Gly Val Leu Gly Gly Ala Gly Gln Phe Pro Leu Gly Gly Val Ala
            660                 665                 670

Ala Arg Pro Gly Phe Gly Leu Ser Pro Ile Phe Pro Gly Gly Ala Cys
    675                 680                 685

Leu Gly Lys Ala Cys Gly Arg Lys Arg Lys
    690                 695

<210> SEQ ID NO 4
<211> LENGTH: 1983
<212> TYPE: DNA
<213> ORGANISM: ARTIFICIAL
<220> FEATURE:
<223> OTHER INFORMATION: Synthetic polynucleotide sequence encoding
      human tropolelastin

<400> SEQUENCE: 4
atgggtggcg ttccgggtgc tgttccgggt ggcgttccgg tggtgtatt ctacccaggc        60 gcgggtttcg gtgctgttcc gggtggcgtt gcagacgcag ctgctgcgta caaagcggca      120
aaggcaggtg cgggtctggg cggggtacca ggtgttggcg gtctgggtgt atctgctggc      180
gcagttgttc gcagccgggt gcaggtgta aaaccgggca agttccagg tgttggtctg        240 ccgggcgtat acccgggttt cggtgctgtt ccgggcgcgc gtttcccagg tgttggtgta      300
ctgccgggcg ttccgaccgg tgcaggtgtt aaaccgaagg caccaggtgt aggcggcgcg      360
ttcgcgggta tccgggtgt tggcccgttc ggtggtccgc agccaggcgt tccgctgggt       420
tacccgatca aagcgccgaa gcttccaggt ggctacggtc tgccgtacac caccggtaaa      480
ctgccgtacg gctacggtcc gggtggcgta gcaggtgctg cgggtaaagc aggctaccca      540
accggtactg tgttggtcc gcaggctgct gcggcagctg cggcgaaggc agcagcaaaa       600

-continued

```
ttcggcgcgg gtgcagcggg tttcggtgct gttccgggcg taggtggtgc tggcgttccg    660
ggtgttccag gtgcgatccc gggcatcggt ggtatcgcag gcgtaggtac tccggcggcc    720
gctgcggctg cggcagctgc ggcgaaagca gctaaatacg gtgcggcagc aggcctggtt    780
ccgggtggtc caggcttcgg tccgggtgtt gtaggcgttc cgggtttcgg tgctgttccg    840
ggcgtaggtg ttccaggtgc gggcatcccg gttgtaccgg gtgcaggtat cccgggcgct    900
gcgggtttcg gtgctgtatc cccggaagcg gcagctaagg ctgctgcgaa agctgcgaaa    960
tacggagctc gtccgggcgt tggtgttggt ggcatcccga cctacggtgt aggtgcaggc   1020
ggtttcccag gtttcggcgt tggtgttggt ggcatcccgg gtgtagctgg tgttccgtct   1080
gttggtggcg taccgggtgt tggtggcgtt ccaggtgtag gtatctcccc ggaagcgcag   1140
gcagctgcgg cagctaaagc agcgaagtac ggcgttggta ctccggcggc agcagctgct   1200
aaagcagcgg ctaaagcagc gcagttcgga ctagttccgg gcgtaggtgt tgcgccaggt   1260
gttggcgtag caccgggtgt tggtgttgct ccgggcgtag gtctggcacc gggtgttggc   1320
gttgcaccag gtgtaggtgt tgcgccgggc gttggtgtag caccgggtat cggtccgggt   1380
ggcgttgcgg ctgctgcgaa atctgctgcg aaggttgctg cgaaagcgca gctgcgtgca   1440
gcagctggtc tgggtgcggg catcccaggt ctgggtgtag gtgttggtgt tccgggcctg   1500
ggtgtaggtg caggggtacc gggcctgggt gttggtgcag gcgttccggg tttcggtgct   1560
gttccgggcg cgctggctgc tgcgaaagcg gcgaaatacg gtgctgttcc gggtgtactg   1620
ggcggtctgg gtgctctggg cggtgttggt atcccgggcg gtgttgtagg tgcaggccca   1680
gctgcagctg ctgctgcggc aaaggcagcg gcgaaagcag ctcagttcgg tctggttggt   1740
gcagcaggtc tgggcggtct gggtgttggc ggtctgggtg taccgggcgt tggtggtctg   1800
ggtggcatcc cgccggcggc ggcagctaaa gcggctaaat acggtgcagc aggtctgggt   1860
ggcgttctgg gtggtgctgg tcagttccca ctgggcggtg tagcggcacg tccgggtttc   1920
ggtctgtccc cgatcttccc aggcggtgca tgcctgggta aagcttgcgg ccgtaaacgt   1980
aaa                                                                 1983
```

<210> SEQ ID NO 5
<211> LENGTH: 660
<212> TYPE: PRT
<213> ORGANISM: HUMAN

<400> SEQUENCE: 5

| Met | Gly | Gly | Val | Pro | Gly | Ala | Val | Pro | Gly | Gly | Val | Pro | Gly | Gly | Val |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Phe Tyr Pro Gly Ala Gly Phe Gly Ala Val Pro Gly Gly Val Ala Asp
            20                  25                  30

Ala Ala Ala Ala Tyr Lys Ala Ala Lys Ala Gly Ala Gly Leu Gly Gly
        35                  40                  45

Val Pro Gly Val Gly Gly Leu Gly Val Ser Ala Gly Ala Val Val Pro
    50                  55                  60

Gln Pro Gly Ala Gly Val Lys Pro Gly Lys Val Pro Gly Val Gly Leu
65                  70                  75                  80

Pro Gly Val Tyr Pro Gly Phe Gly Ala Val Pro Gly Ala Arg Phe Pro
                85                  90                  95

Gly Val Gly Val Leu Pro Gly Val Pro Thr Gly Ala Gly Val Lys Pro
            100                 105                 110

Lys Ala Pro Gly Val Gly Gly Ala Phe Ala Gly Ile Pro Gly Val Gly

-continued

```
            115                 120                 125
Pro Phe Gly Gly Pro Gln Pro Gly Val Pro Leu Gly Tyr Pro Ile Lys
    130                 135                 140
Ala Pro Lys Leu Pro Gly Gly Tyr Gly Leu Pro Tyr Thr Thr Gly Lys
145                 150                 155                 160
Leu Pro Tyr Gly Tyr Gly Pro Gly Val Ala Ala Gly Lys Ala
                165                 170                 175
Gly Tyr Pro Thr Gly Thr Gly Val Gly Pro Gln Ala Ala Ala Ala
                180                 185                 190
Ala Ala Lys Ala Ala Ala Lys Phe Gly Ala Gly Ala Ala Gly Phe Gly
                195                 200                 205
Ala Val Pro Gly Val Gly Gly Ala Gly Val Pro Gly Val Pro Gly Ala
    210                 215                 220
Ile Pro Gly Ile Gly Gly Ile Ala Gly Val Gly Thr Pro Ala Ala Ala
225                 230                 235                 240
Ala Ala Ala Ala Ala Ala Lys Ala Ala Lys Tyr Gly Ala Ala Ala
                245                 250                 255
Gly Leu Val Pro Gly Gly Pro Gly Phe Gly Pro Gly Val Val Gly Val
            260                 265                 270
Pro Gly Phe Gly Ala Val Pro Gly Val Gly Val Pro Gly Ala Gly Ile
            275                 280                 285
Pro Val Val Pro Gly Ala Gly Ile Pro Gly Ala Ala Gly Phe Gly Ala
        290                 295                 300
Val Ser Pro Glu Ala Ala Ala Lys Ala Ala Ala Lys Ala Ala Lys Tyr
305                 310                 315                 320
Gly Ala Arg Pro Gly Val Gly Val Gly Gly Ile Pro Thr Tyr Gly Val
                325                 330                 335
Gly Ala Gly Phe Phe Pro Gly Phe Gly Val Gly Val Gly Gly Ile Pro
                340                 345                 350
Gly Val Ala Gly Val Pro Ser Val Gly Gly Val Pro Gly Val Gly Gly
            355                 360                 365
Val Pro Gly Val Gly Ile Ser Pro Glu Ala Gln Ala Ala Ala Ala
    370                 375                 380
Lys Ala Ala Lys Tyr Gly Val Gly Thr Pro Ala Ala Ala Ala Lys
385                 390                 395                 400
Ala Ala Ala Lys Ala Ala Gln Phe Gly Leu Val Pro Gly Val Gly Val
                405                 410                 415
Ala Pro Gly Val Gly Val Ala Pro Gly Val Gly Val Ala Pro Gly Val
            420                 425                 430
Gly Leu Ala Pro Gly Val Gly Val Ala Pro Gly Val Gly Val Ala Pro
            435                 440                 445
Gly Val Gly Val Ala Pro Gly Ile Gly Pro Gly Gly Val Ala Ala Ala
        450                 455                 460
Ala Lys Ser Ala Ala Lys Val Ala Ala Lys Ala Gln Leu Arg Ala Ala
465                 470                 475                 480
Ala Gly Leu Gly Ala Gly Ile Pro Gly Leu Gly Val Gly Val Gly Val
                485                 490                 495
Pro Gly Leu Gly Val Gly Ala Gly Val Pro Gly Leu Gly Val Gly Ala
            500                 505                 510
Gly Val Pro Gly Phe Gly Ala Val Pro Gly Ala Leu Ala Ala Ala Lys
            515                 520                 525
Ala Ala Lys Tyr Gly Ala Val Pro Gly Val Leu Gly Gly Leu Gly Ala
    530                 535                 540
```

```
Leu Gly Gly Val Gly Ile Pro Gly Gly Val Gly Ala Gly Pro Ala
545                 550                 555                 560

Ala Ala Ala Ala Ala Lys Ala Ala Lys Ala Ala Gln Phe Gly
            565                 570                 575

Leu Val Gly Ala Ala Gly Leu Gly Gly Leu Gly Val Gly Gly Leu Gly
                580                 585                 590

Val Pro Gly Val Gly Gly Leu Gly Gly Ile Pro Pro Ala Ala Ala
            595                 600                 605

Lys Ala Ala Lys Tyr Gly Ala Ala Gly Leu Gly Gly Val Leu Gly Gly
            610                 615                 620

Ala Gly Gln Phe Pro Leu Gly Gly Val Ala Ala Arg Pro Gly Phe Gly
625                 630                 635                 640

Leu Ser Pro Ile Phe Pro Gly Gly Ala Cys Leu Gly Lys Ala Cys Gly
                645                 650                 655

Arg Lys Arg Lys
            660

<210> SEQ ID NO 6
<211> LENGTH: 441
<212> TYPE: DNA
<213> ORGANISM: ARTIFICIAL
<220> FEATURE:
<223> OTHER INFORMATION: Synthetic polynucleotide sequence encoding
      human tropelelastin

<400> SEQUENCE: 6
tccgccatgg gaggtgttcc gggcgcgctg gctgctgcga aagcggcgaa atacggtgca     60
gcggttccgg tgtactgggt cggtctgggt gctctgggcg tgttggtat cccgggcggt    120 gttgtaggtg caggcccagc tgcagctgct gctgcggcaa aggcagcggc gaaagcagct   180
cagttcggtc tggttggtgc agcaggtgtg ggcggtctgg tgttggcgg tctgggtgta    240 ccgggcgttg gtggtctggg tggcatcccg ccggcggcgg cagctaaagc ggctaaatac   300
ggtgcagcag gtctgggtgg cgttctgggt ggtgctggtc agttcccact gggcggtgta   360
gcggcacgtc cgggtttcgg tctgtccccg atcttcccag gcggtgcatg cctgggtaaa   420
gcttgcggcc gtaaacgtaa a                                              441

<210> SEQ ID NO 7
<211> LENGTH: 147
<212> TYPE: PRT
<213> ORGANISM: HUMAN

<400> SEQUENCE: 7

Ser Ala Met Gly Gly Val Pro Gly Ala Leu Ala Ala Lys Ala Ala
1               5                   10                  15

Lys Tyr Gly Ala Ala Val Pro Gly Val Leu Gly Gly Leu Gly Ala Leu
            20                  25                  30

Gly Gly Val Gly Ile Pro Gly Gly Val Gly Ala Gly Pro Ala Ala
            35                  40                  45

Ala Ala Ala Ala Ala Lys Ala Ala Lys Ala Ala Gln Phe Gly Leu
        50                  55                  60

Val Gly Ala Ala Gly Leu Gly Gly Leu Gly Val Gly Gly Leu Gly Val
65                  70                  75                  80

Pro Gly Val Gly Gly Leu Gly Gly Ile Pro Pro Ala Ala Ala Lys
                85                  90                  95

Ala Ala Lys Tyr Gly Ala Ala Gly Leu Gly Gly Val Leu Gly Gly Ala
```

-continued

```
                   100                 105                 110
Gly Gln Phe Pro Leu Gly Gly Val Ala Ala Arg Pro Gly Phe Gly Leu
               115                 120                 125

Ser Pro Ile Phe Pro Gly Gly Ala Cys Leu Gly Lys Ala Cys Gly Arg
           130                 135                 140

Lys Arg Lys
145

<210> SEQ ID NO 8
<211> LENGTH: 600
<212> TYPE: DNA
<213> ORGANISM: ARTIFICIAL
<220> FEATURE:
<223> OTHER INFORMATION: Synthetic polynucleotide sequence encoding
      human tropolelastin

<400> SEQUENCE: 8
tccgccatgg gagctctggt aggcctgggc gtaccgggcc tgggtgttgg tgcaggcgtt        60
ccgggtttcg gtgctggcgc ggacgaaggt gtacgtcgtt ccctgtctcc agaactgcgt       120
gaaggtgacc cgtcctcttc ccagcacctg ccgtctaccc cgtcctctcc acgtgttccg       180
ggcgcgctgg ctgctgcgaa agcggcgaaa tacggtgcag cggttccggg tgtactgggc       240
ggtctgggtg ctctgggcgg tgttggtatc ccgggcggtg ttgtaggtgc aggcccagct       300
gcagctgctg ctgcggcaaa ggcagcggcg aaagcagctc agttcggtct ggttggtgca       360
gcaggtctgg gcggtctggg tgttggcggt ctgggtgtac gggcgttgg tggtctgggt        420 ggcatcccgc cggcggcggc agctaaagcg ctaaatacg gtgcagcagg tctgggtggc        480
gttctgggtg tgctggtca gttcccactg ggcggtgtag cggcacgtcc gggtttcggt        540
ctgtccccga tcttcccagg cggtgcatgc ctgggtaaag cttgcggccg taaacgtaaa       600

<210> SEQ ID NO 9
<211> LENGTH: 200
<212> TYPE: PRT
<213> ORGANISM: HUMAN

<400> SEQUENCE: 9

Ser Ala Met Gly Ala Leu Val Gly Leu Gly Val Pro Gly Leu Gly Val
1               5                  10                  15

Gly Ala Gly Val Pro Gly Phe Gly Ala Gly Ala Asp Glu Gly Val Arg
               20                  25                  30

Arg Ser Leu Ser Pro Glu Leu Arg Glu Gly Asp Pro Ser Ser Ser Gln
           35                  40                  45

His Leu Pro Ser Thr Pro Ser Ser Pro Arg Val Pro Gly Ala Leu Ala
       50                  55                  60

Ala Ala Lys Ala Ala Lys Tyr Gly Ala Ala Val Pro Gly Val Leu Gly
65                  70                  75                  80

Gly Leu Gly Ala Leu Gly Gly Val Gly Ile Pro Gly Gly Val Val Gly
                   85                  90                  95

Ala Gly Pro Ala Ala Ala Ala Ala Ala Lys Ala Ala Ala Lys Ala
               100                 105                 110

Ala Gln Phe Gly Leu Val Gly Ala Ala Gly Leu Gly Gly Leu Gly Val
           115                 120                 125

Gly Gly Leu Gly Val Pro Gly Val Gly Gly Leu Gly Gly Ile Pro Pro
       130                 135                 140

Ala Ala Ala Ala Lys Ala Ala Lys Tyr Gly Ala Ala Gly Leu Gly Gly
145                 150                 155                 160
```

```
Val Leu Gly Gly Ala Gly Gln Phe Pro Leu Gly Gly Val Ala Ala Arg
            165                 170                 175

Pro Gly Phe Gly Leu Ser Pro Ile Phe Pro Gly Gly Ala Cys Leu Gly
            180                 185                 190

Lys Ala Cys Gly Arg Lys Arg Lys
            195                 200

<210> SEQ ID NO 10
<211> LENGTH: 60
<212> TYPE: PRT
<213> ORGANISM: HUMAN

<400> SEQUENCE: 10

Gly Ile Pro Pro Ala Ala Ala Lys Ala Ala Lys Tyr Gly Ala Ala
1               5                   10                  15

Gly Leu Gly Gly Val Leu Gly Gly Ala Gly Gln Phe Pro Leu Gly Gly
                20                  25                  30

Val Ala Ala Arg Pro Gly Phe Gly Leu Ser Pro Ile Phe Pro Gly Gly
                35                  40                  45

Ala Cys Leu Gly Lys Ala Cys Gly Arg Lys Arg Lys
            50                  55                  60

<210> SEQ ID NO 11
<211> LENGTH: 47
<212> TYPE: PRT
<213> ORGANISM: HUMAN

<400> SEQUENCE: 11

Gly Ala Ala Gly Leu Gly Gly Val Leu Gly Gly Ala Gly Gln Phe Pro
1               5                   10                  15

Leu Gly Gly Val Ala Ala Arg Pro Gly Phe Gly Leu Ser Pro Ile Phe
                20                  25                  30

Pro Gly Gly Ala Cys Leu Gly Lys Ala Cys Gly Arg Lys Arg Lys
            35                  40                  45

<210> SEQ ID NO 12
<211> LENGTH: 34
<212> TYPE: PRT
<213> ORGANISM: HUMAN

<400> SEQUENCE: 12

Gly Ala Asp Glu Gly Val Arg Arg Ser Leu Ser Pro Glu Leu Arg Glu
1               5                   10                  15

Gly Asp Pro Ser Ser Ser Gln His Leu Pro Ser Thr Pro Ser Ser Pro
                20                  25                  30

Arg Val

<210> SEQ ID NO 13
<211> LENGTH: 34
<212> TYPE: PRT
<213> ORGANISM: HUMAN

<400> SEQUENCE: 13

Gly Ala Asp Glu Gly Val Arg Arg Ser Leu Ser Pro Glu Leu Arg Glu
1               5                   10                  15

Gly Asp Pro Ser Ser Ser Gln His Leu Pro Ser Thr Pro Ser Ser Pro
                20                  25                  30

Arg Phe
```

```
<210> SEQ ID NO 14
<211> LENGTH: 216
<212> TYPE: PRT
<213> ORGANISM: HUMAN

<400> SEQUENCE: 14

Ala Ala Ala Gly Leu Gly Ala Gly Ile Pro Gly Leu Gly Val Gly Val
1               5                   10                  15

Gly Val Pro Gly Leu Gly Val Gly Ala Gly Val Pro Gly Leu Gly Val
            20                  25                  30

Gly Ala Gly Val Pro Gly Phe Gly Ala Gly Ala Asp Glu Gly Val Arg
        35                  40                  45

Arg Ser Leu Ser Pro Glu Leu Arg Glu Gly Asp Pro Ser Ser Ser Gln
    50                  55                  60

His Leu Pro Ser Thr Pro Ser Ser Pro Arg Val Pro Gly Ala Leu Ala
65                  70                  75                  80

Ala Ala Lys Ala Ala Lys Tyr Gly Ala Ala Val Pro Gly Val Leu Gly
                85                  90                  95

Gly Leu Gly Ala Leu Gly Gly Val Gly Ile Pro Gly Gly Val Val Gly
            100                 105                 110

Ala Gly Pro Ala Ala Ala Ala Ala Ala Lys Ala Ala Ala Lys Ala
            115                 120                 125

Ala Gln Phe Gly Leu Val Gly Ala Ala Gly Leu Gly Gly Leu Gly Val
        130                 135                 140

Gly Gly Leu Gly Val Pro Gly Val Gly Gly Leu Gly Gly Ile Pro Pro
145                 150                 155                 160

Ala Ala Ala Ala Lys Ala Ala Lys Tyr Gly Ala Ala Gly Leu Gly Gly
                165                 170                 175

Val Leu Gly Gly Ala Gly Gln Phe Pro Leu Gly Gly Val Ala Ala Arg
            180                 185                 190

Pro Gly Phe Gly Leu Ser Pro Ile Phe Pro Gly Gly Ala Cys Leu Gly
        195                 200                 205

Lys Ala Cys Gly Arg Lys Arg Lys
    210                 215

<210> SEQ ID NO 15
<211> LENGTH: 183
<212> TYPE: PRT
<213> ORGANISM: HUMAN

<400> SEQUENCE: 15

Ala Ala Ala Gly Leu Gly Ala Gly Ile Pro Gly Leu Gly Val Gly Val
1               5                   10                  15

Gly Val Pro Gly Leu Gly Val Gly Ala Gly Val Pro Gly Leu Gly Val
            20                  25                  30

Gly Ala Gly Val Pro Gly Phe Gly Ala Val Pro Gly Ala Leu Ala Ala
        35                  40                  45

Ala Lys Ala Ala Lys Tyr Gly Ala Ala Val Pro Gly Val Leu Gly Gly
    50                  55                  60

Leu Gly Ala Leu Gly Gly Val Gly Ile Pro Gly Gly Val Val Gly Ala
65                  70                  75                  80

Gly Pro Ala Ala Ala Ala Ala Ala Lys Ala Ala Lys Ala Ala
                85                  90                  95

Gln Phe Gly Leu Val Gly Ala Ala Gly Leu Gly Gly Leu Gly Val Gly
            100                 105                 110
```

```
Gly Leu Gly Val Pro Gly Val Gly Gly Leu Gly Gly Ile Pro Pro Ala
        115                 120                 125

Ala Ala Ala Lys Ala Ala Lys Tyr Gly Ala Ala Gly Leu Gly Gly Val
        130                 135                 140

Leu Gly Gly Ala Gly Gln Phe Pro Leu Gly Gly Val Ala Ala Arg Pro
145                 150                 155                 160

Gly Phe Gly Leu Ser Pro Ile Phe Pro Gly Gly Ala Cys Leu Gly Lys
                165                 170                 175

Ala Cys Gly Arg Lys Arg Lys
            180

<210> SEQ ID NO 16
<211> LENGTH: 30
<212> TYPE: DNA
<213> ORGANISM: ARTIFICIAL
<220> FEATURE:
<223> OTHER INFORMATION: Synthetic polynucleotide sequence encoding
      human tropolelastin

<400> SEQUENCE: 16
cgggtttcgg tgctgttccg ggcgcgctgg                                    30
```